(12) United States Patent
Koizumi et al.

(10) Patent No.: US 9,241,636 B2
(45) Date of Patent: Jan. 26, 2016

(54) TUMOR SITE OR PARATHYROID GLAND IDENTIFICATION DEVICE AND METHOD

(71) Applicant: KYOTO PREFECTURAL PUBLIC UNIVERSITY CORPORATION, Kyoto-shi, Kyoto (JP)

(72) Inventors: Noriaki Koizumi, Kyoto (JP); Tetsuro Takamatsu, Kyoto (JP); Yoshinori Harada, Kyoto (JP); Eigo Otsuji, Kyoto (JP)

(73) Assignee: Kyoto Prefectural Public University Corporation, Kyoto (JP)

( * ) Notice: Subject to any disclaimer, the term of this patent is extended or adjusted under 35 U.S.C. 154(b) by 116 days.

(21) Appl. No.: 14/142,384

(22) Filed: Dec. 27, 2013

(65) Prior Publication Data
US 2014/0163391 A1 Jun. 12, 2014

Related U.S. Application Data

(63) Continuation-in-part of application No. PCT/JP2012/066609, filed on Jun. 28, 2012.

(30) Foreign Application Priority Data

Jun. 29, 2011 (JP) ................................ 2011-143709

(51) Int. Cl.
*A61B 5/00* (2006.01)
*A61B 1/00* (2006.01)
(Continued)

(52) U.S. Cl.
CPC ........... *A61B 5/0071* (2013.01); *A61B 1/00186* (2013.01); *A61B 1/0646* (2013.01);
(Continued)

(58) Field of Classification Search
CPC ........................... A61B 5/0059; A61B 5/0071
See application file for complete search history.

(56) References Cited

U.S. PATENT DOCUMENTS 8,948,851 B2 * 2/2015 Leblond et al. ............... 600/476
2003/0167033 A1 * 9/2003 Chen et al. ...................... 604/20
(Continued)

FOREIGN PATENT DOCUMENTS

| JP | 64-009345 A | 1/1989 |
|---|---|---|
| JP | 2006-124372 A | 5/2006 |

(Continued)

OTHER PUBLICATIONS

Bagdonas et al., *Photochemistry and Photobiology*, 72(2): 186-192 (2000).

(Continued)

*Primary Examiner* — Peter Luong
(74) *Attorney, Agent, or Firm* — Leydig, Voit & Mayer, Ltd.

(57) ABSTRACT

The present invention provides a device for identifying a tumor site in a subject, the device spectroscopically detecting fluorescence of protoporphyrins present in the tumor site,
the protoporphyrins being protoporphyrin IX (PpIX) and photo-protoporphyrin (PPp), and
the device comprising:
a light irradiation unit that converts part of PpIX into PPp;
a spectroscopy unit that separates PpIX fluorescence and PPp fluorescence:
a spectroscopy detection unit that detects the relative fluorescence intensity of the PpIX fluorescence and the PPp fluorescence; and
a tumor discrimination unit that discriminates between the tumor site and a non-tumor site based on the relative fluorescence intensity of PpIX and PPp.

20 Claims, 23 Drawing Sheets

(51) Int. Cl.
*A61B 1/06* (2006.01)
*G01N 21/64* (2006.01)

(52) U.S. Cl.
CPC ............... *A61B5/0084* (2013.01); *A61B 5/418* (2013.01); *A61B 5/6847* (2013.01); *G01N 21/6458* (2013.01); *G01N 21/6486* (2013.01); *A61B 5/0091* (2013.01); *G01N 2021/6421* (2013.01)

(56) References Cited

U.S. PATENT DOCUMENTS

2008/0108701 A1   5/2008   Okura et al.
2009/0202119 A1   8/2009   Hefti et al.

FOREIGN PATENT DOCUMENTS

JP   2009-148568 A   7/2009
JP   2010-240078 A   10/2010

OTHER PUBLICATIONS

Ichikura et al., *Annals of Surgery*, 249(6): 942-947 (2009).
Kriegmair et al., *The Journal of Urology*, 155: 105-110 (1996).
Mayinger et al., *Gastrointestinal Endoscopy*, 50(2): 242-246 (1999).
Moan et al., *Int. J. Cancer*, 70(1): 90-97 (1997).
Murayama et al., *Int. J. Cancer*, 125(10): 2256-2263 (2009).
Prosst et al., *Surgical Endoscopy*, 20: 1488-1492 (2006).
Stummer et al., *Neurosurgery*, 42(3): 518-526 (1998).
Japanese Patent Office, International Search Report in International Patent Application No. PCT/JP2012/066609 (Jul. 24, 2012).
Cottrell et al., *Clinical Cancer Research* 14(14): 4475-4483 (Jul. 15, 2008).
Konig et al., *Medical Laser Application*, 21(4): 291-297 (Nov. 15, 2006).
Streckyte et al., *SPIE Proceedings*, 2325 (Photodynamic Therapy of Cancer II): 58-65 (1994).
European Patent Office, Supplementary European Search Report in European Patent Application 12804029.2 (Mar. 10, 2015).

* cited by examiner

TUMOR SITE OR PARATHYROID GLAND IDENTIFICATION DEVICE AND METHOD

CROSS-REFERENCE TO RELATED APPLICATIONS

The present application is a continuation application of International Application No. PCT/JP2012/066609, filed on Jun. 28, 2012, which claims priority to Japanese Patent Application No. 2011-143709, filed on Jun. 28, 2011. The contents of these applications are incorporated herein by reference in their entirety.

TECHNICAL FIELD

The present invention relates to a device and method for identifying a tumor site. The present invention also relates to a device and method for identifying parathyroid gland.

BACKGROUND ART

Lymph node metastasis is an important prognostic factor in gastrointestinal cancers, such as gastric cancer and colon cancer. Accurate diagnosis of the presence of lymph node metastasis is essential to determine appropriate treatment for patients.

For example, the necessity of postoperative adjuvant therapy for many gastrointestinal cancers is determined by the presence of lymph node metastasis (NPL 1 and NPL 2). In particular, when the diagnosis of gastric cancer with intraoperative sentinel lymph node biopsy shows that there is no metastasis, surgery with reduced lymph node dissection may be selected (NPL 3). For these reasons, rapid and accurate diagnosis of lymph node metastasis would be clinically very useful.

However, no diagnostic technique has been established at present to replace conventional histopathological diagnosis. Routine histopathological diagnosis of lymph node metastasis is performed only on samples obtained from only a single or a few sections; therefore, it is possible to miss some cases of micrometastasis, and its diagnostic accuracy is not sufficient (NPL 4). Moreover, intraoperative rapid diagnosis takes at least 20 to 30 minutes before the diagnosis. It is thus necessary to establish a new, more accurate and rapid approach.

Photodynamic technology using 5-aminolevulinic acid (5-ALA) is currently applied for cancer detection in a wide region including the gastrointestinal region (NPL 5, NPL 6, and NPL 7). 5-ALA is a kind of endogenous amino acid, and when exogenous 5-ALA is administered, protoporphyrin IX (PpIX), which is a metabolite of 5-ALA, accumulates in cancer cells due to the difference in the activity of metabolic enzymes. The principle of this technology is to detect PpIX, which is a fluorescent material, for cancer diagnosis. The present inventors' group reported very excellent results of the diagnosis of lymph node metastasis in a murine model of rectal cancer by a method using 5-ALA-induced PpIX fluorescence (NPL 4). This was the first report on photodynamic diagnosis using 5-ALA for lymph node metastasis of gastrointestinal cancer.

Photodynamic technology using 5-aminolevulinic acid (5-ALA) is currently applied for parathyroid gland detection (NPL 10).

However, lymph nodes in the human body are wrapped in connective tissues. In other words, lymph nodes in the human body contains rich connective tissues. Connective tissues (e.g., fat, collagen, etc.) emit strong autofluorescence in the blue to green wavelength range upon irradiation with blue excitation light. This autofluorescence interferes with the detection of PpIX fluorescence.

It is known that PpIX is photobleached by light irradiation, and that a photooxidation reaction occurs during photobleaching to convert PpIX into another substance called photo-protoporphyrin (PPp) (NPL 8). PpIX has a fluorescence peak at 635 nm, while PPp has another fluorescence peak at about 675 nm (NPL 9).

CITATION LIST

Non-Patent Literature

NPL 1: "Japanese Gastric Cancer Treatment Guidelines (Ver. 3)," edited by Japanese Gastric Cancer Association, Kanehara & Co., Ltd.
NPL 2: "JSCCR Guidelines 2010 for the Treatment of Colorectal Cancer," edited by Japanese Society for Cancer of the Colon and Rectum, Kanehara & Co., Ltd.
NPL 3: Ichikura T, et al., Ann Surg, 2009 June; 249(6):942-7
NPL 4: Murayama Y, et al., Int J Cancer, 2009 Nov. 15; 125(10):2256-63
NPL 5: Stummer W, et al., Neurosurgery, 1998 March; 42(3): 518-25
NPL 6: Kriegmair M, et al., J Urol, 1996 January; 155(1): 105-9
NPL 7: Mayinger B, et al., Gastrointest Endosc, 1999 August; 50(2):242-6
NPL 8: Moan J, et al., Int J Cancer, 1997 Jan. 6; 70(1):90-7
NPL 9: Bagdonas S, et al., Photochem Photobiol, 2000 August; 72(2):186-92
NPL 10: Prosst R L, et al., Surg Endosc, 2006; 20: 1488-92

SUMMARY OF INVENTION

Technical Problem

Identification of tumor sites, particularly tumor sites covered with or in coexistence with connective tissues, such as lymph nodes, in clinical applications requires the elimination of autofluorescence of endogenous tissues. Similar problems reside in identification of parathyroid glands.

A primary object of the present invention is to establish a method for specifically detecting fluorescence of porphyrins, and to increase the speed and accuracy of the diagnosis of tumor sites, including lymph node metastasis, or parathyroid glands in clinical practice.

Solution to Problem

PpIX is converted into another substance called photo-protoporphyrin (PPp) by irradiation with excitation light. PpIX has a fluorescence peak at 635 nm, whereas PPp has another fluorescence peak at about 675 nm. Since PpIX and PPp have different fluorescence peaks, the conversion from PpIX to PPp can be observed as spectral waveform changes over time.

This conversion can also be observed pictorially by using ratio images of two spectroscopic images at 635 nm and 675 nm corresponding to PpIX and PPp, respectively.

Focusing on this conversion, the present inventors found that the localization of PpIX can be specifically identified by ratio imaging based on the photoconversion (photobleaching) of PpIX.

The present invention provides the following device and method for detecting a tumor site.

Item 1. A device for identifying a tumor site in a subject, the device spectroscopically detecting fluorescence of protoporphyrins present in the tumor site,
the protoporphyrins being protoporphyrin IX (PpIX) and photo-protoporphyrin (PPp), and
the device comprising:
a light irradiation unit that converts part of PpIX into PPp;
a spectroscopy unit that separates PpIX fluorescence and PPp fluorescence:
a spectroscopy detection unit that detects the relative fluorescence intensity of the PpIX fluorescence and the PPp fluorescence; and
a tumor discrimination unit that discriminates between the tumor site and a non-tumor site based on the relative fluorescence intensity of PpIX and PPp.

Item 2. The device according to Item 1, wherein the light irradiation unit comprises a light source and a light source optical fiber for guiding excitation light from the light source to the subject.

Item 3. The device according to Item 1 or 2, wherein the spectroscopy detection unit comprises a means for detecting PpIX-derived fluorescence at around 635 nm, and a means for detecting PPp-derived fluorescence at around 675 nm.

Item 4. The device according to any one of Items 1 to 3, comprising a spectroscopy optical fiber for guiding the PpIX fluorescence and the PPp fluorescence to the spectroscopy unit.

Item 5. The device according to any one of Items 1 to 4, further comprising a display unit that displays information regarding the tumor discrimination results from the tumor discrimination unit, as image information corresponding to the position of the discriminated tumor site emitting fluorescence in the subject.

Item 6. A method for identifying a tumor site in a subject, comprising the steps of:
irradiating protoporphyrin IX (PpIX) accumulated in the tumor site of the subject with light to convert part of PpIX into photo-protoporphyrin (PPp);
irradiating excitation light for PpIX and PPp;
separating fluorescence emitted from PpIX and PPp, which have been excited with the excitation light, into PpIX fluorescence and PPp fluorescence using a spectroscopy unit;
detecting the relative fluorescence intensity of the PpIX fluorescence and the PPp fluorescence; and
discriminating between the tumor site and a non-tumor site based on the relative fluorescence intensity of PpIX and PPp.

Item 7. The method according to Item 6, wherein the tumor is a tumor metastasized to a sentinel lymph node.

The present invention also provides the following device and method for detecting a parathyroid gland.

Item 8. A device for identifying a parathyroid gland in a subject, the device spectroscopically detecting fluorescence of protoporphyrins present in the parathyroid gland,
the protoporphyrins being protoporphyrin IX (PpIX) and photo-protoporphyrin (PPp), and
the device comprising:
a light irradiation unit that converts part of PpIX into PPp;
a spectroscopy unit that separates PpIX fluorescence and PPp fluorescence:
a spectroscopy detection unit that detects the relative fluorescence intensity of the PpIX fluorescence and the PPp fluorescence; and
a parathyroid gland discrimination unit that discriminates between the parathyroid gland site and another site based on the relative fluorescence intensity of PpIX and PPp.

Item 9. A method for identifying a parathyroid gland in a subject, comprising the steps of:
irradiating protoporphyrin IX (PpIX) accumulated in the parathyroid gland of the subject with light to convert part of PpIX into photo-protoporphyrin (PPp);
irradiating excitation light for PpIX and PPp;
separating fluorescence emitted from PpIX and PPp, which have been excited with the excitation light, into PpIX fluorescence and PPp fluorescence using a spectroscopy unit;
detecting the relative fluorescence intensity of the PpIX fluorescence and the PPp fluorescence; and
discriminating between the parathyroid gland and another site based on the relative fluorescence intensity of PpIX and PPp.

Advantageous Effects of Invention

According to the present invention, a tumor site or a parathyroid gland can be identified accurately and rapidly even in an area with connective tissues (e.g., fat, collagen, etc.), which emit strong autofluorescence in the blue to green wavelength region. For example, the device or method of the present invention facilitates the diagnosis of residual tumor around the tumor site after removal, or the diagnosis of metastasis in dissected lymph nodes. This contributes to improved surgical outcomes.

The device of the present invention can specifically detect a tumor site or a parathyroid gland rapidly and easily, without the need for other complicated equipment, and can be used in an operating room or at the bedside.

The clinical application of the device of the present invention is expected to provide the following advantages:
- The device of the present invention is contributory to intraoperative rapid diagnosis, leading to more accurate and rapid diagnosis.
- When detecting a tumor site, accurate intraoperative diagnosis results in reduction surgery and surgery without residual tumor.

DESCRIPTION OF EMBODIMENTS

Figure 1:
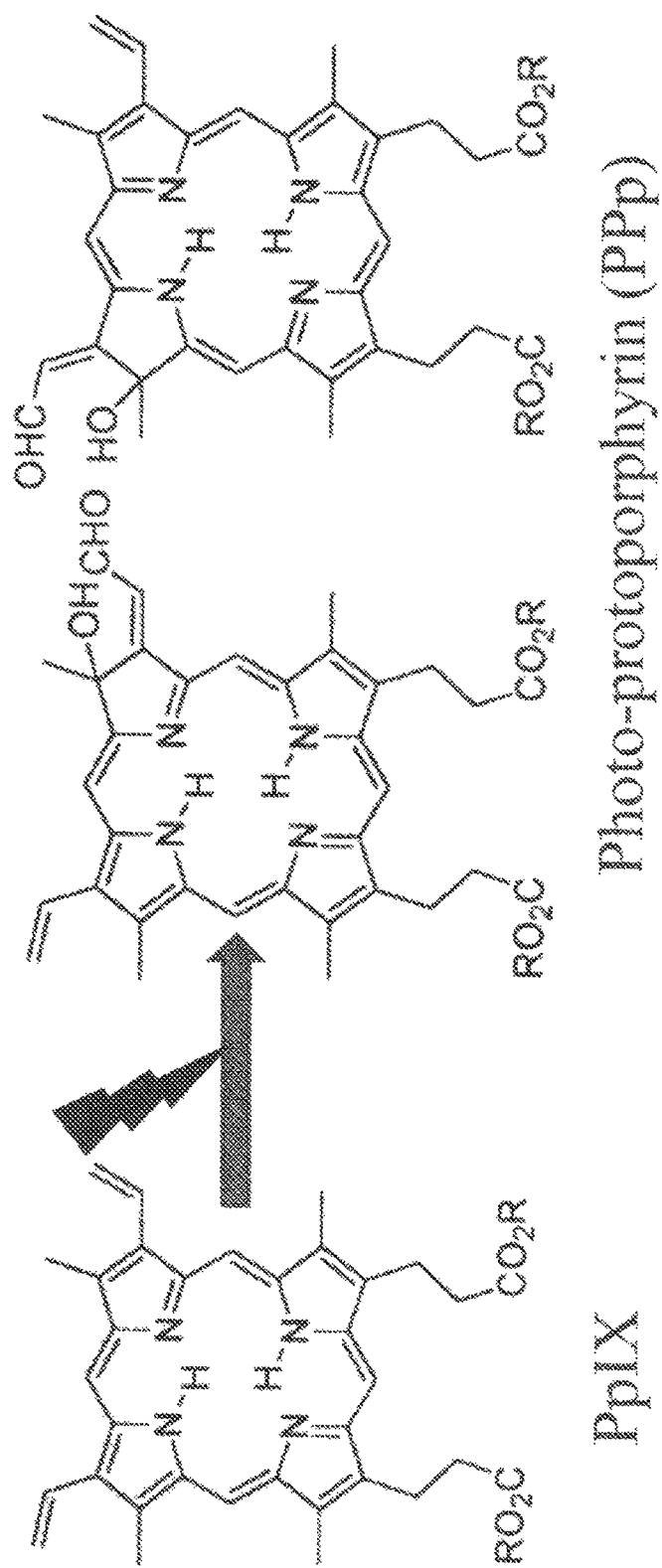
FIG. 1 shows the photoconversion (photooxidation) of PpIX. Cox G S, Krieg M, Whitten D G., J. Am. Chem. Soc., 1982, 104, 6930-6937

When protoporphyrin IX (PpIX) is converted into photoprotoporphyrin (PPp) by light irradiation (FIG. 1), the fluorescence wavelength is shifted to a longer wavelength by about 40 nm. In the present invention, the tumor site or the parathyroid gland can be identified based on the difference in the fluorescence wavelength of PpIX and PPp, without the influence of autofluorescence.

Figure 2:
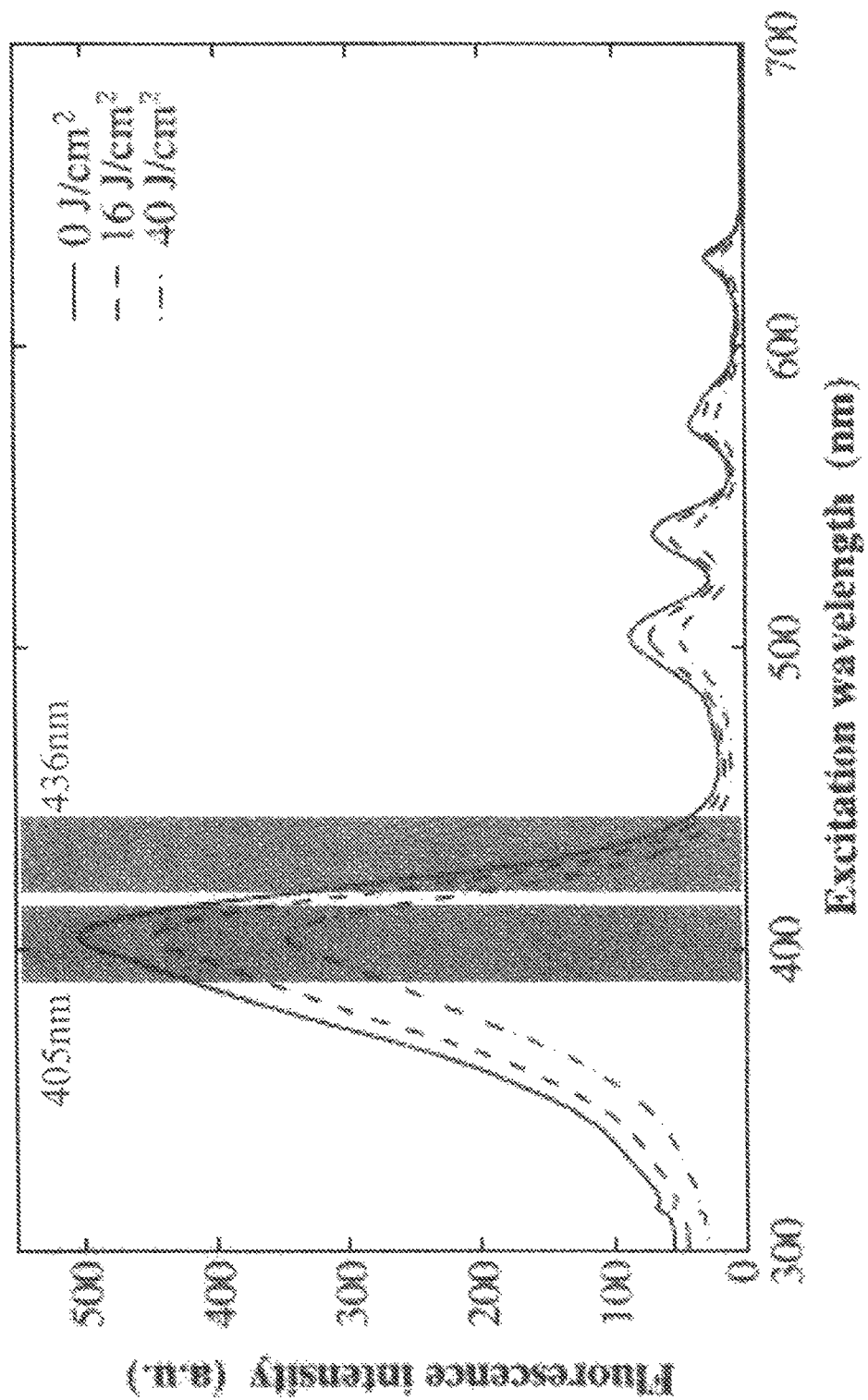
FIG. 2 shows the excitation spectra of PpIX. Ericson M B, Grapengiesser S, Gudmundson F, et al., Laser. Med. Sci., 2003, 18, 56-62
Figure 3:
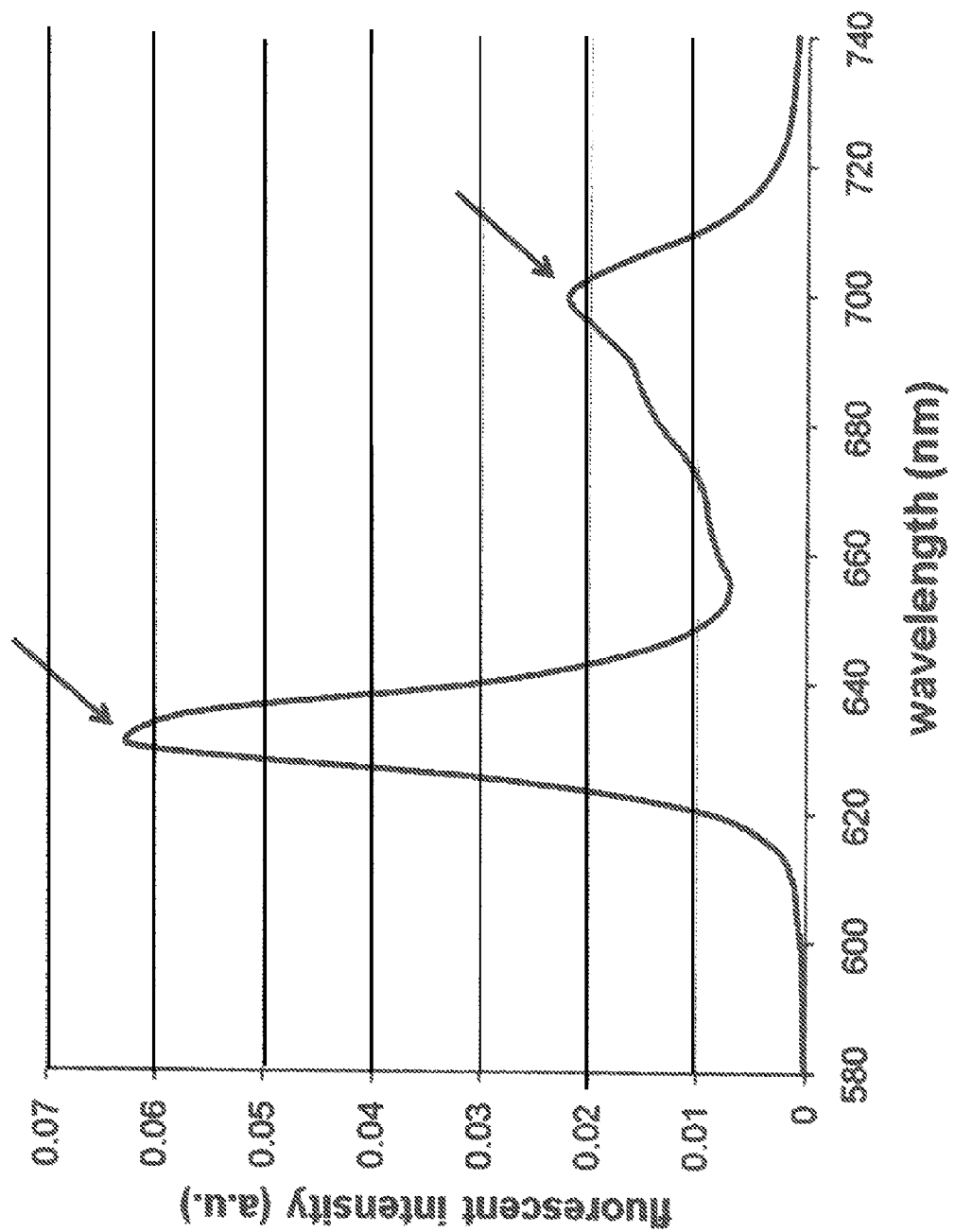
FIG. 3 shows the fluorescence spectrum of PpIX.

PpIX is most excited at an excitation wavelength of around 405 nm (FIG. 2), and the maximum fluorescence emission wavelength is about 635 nm (FIG. 3).

Figure 4:
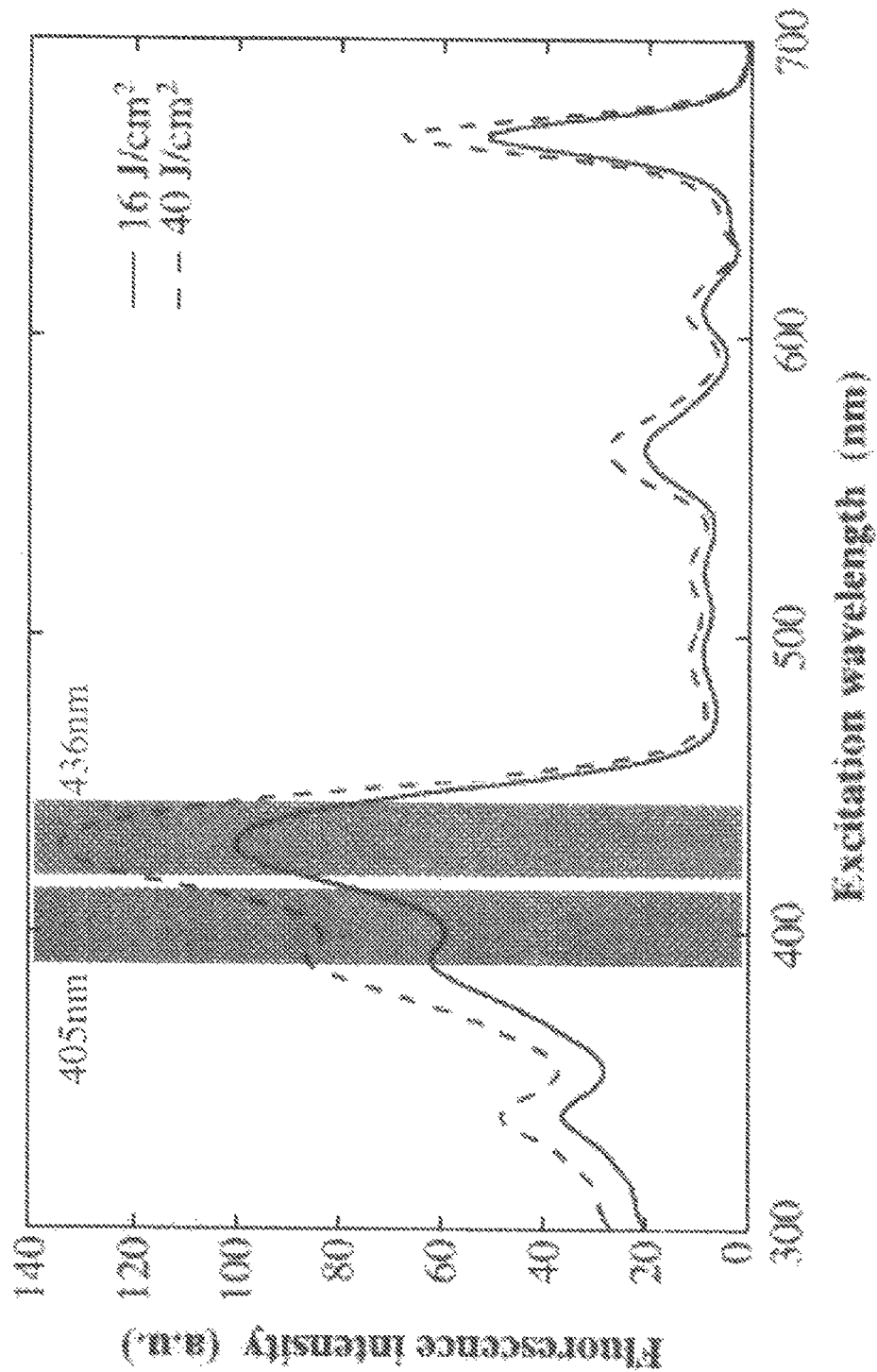
FIG. 4 shows the excitation spectra of PPp. Ericson M B, Grapengiesser S, Gudmundson F, et al., Laser. Med. Sci., 2003, 18, 56-62
Figure 5:
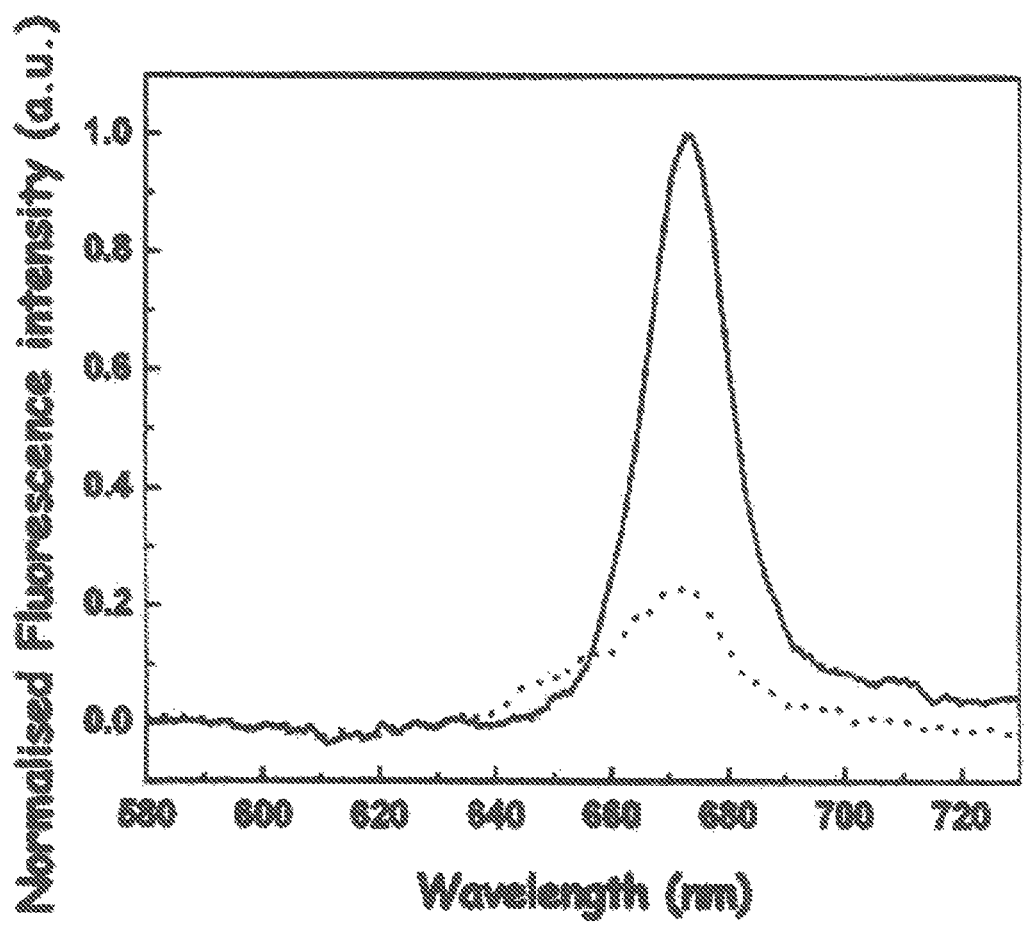
FIG. 5 shows the fluorescence spectrum of PPp.

PPp is most excited at an excitation wavelength of around 436 nm (FIG. 4), and the maximum fluorescence emission wavelength is about 675 nm (FIG. 5).

Figure 6:
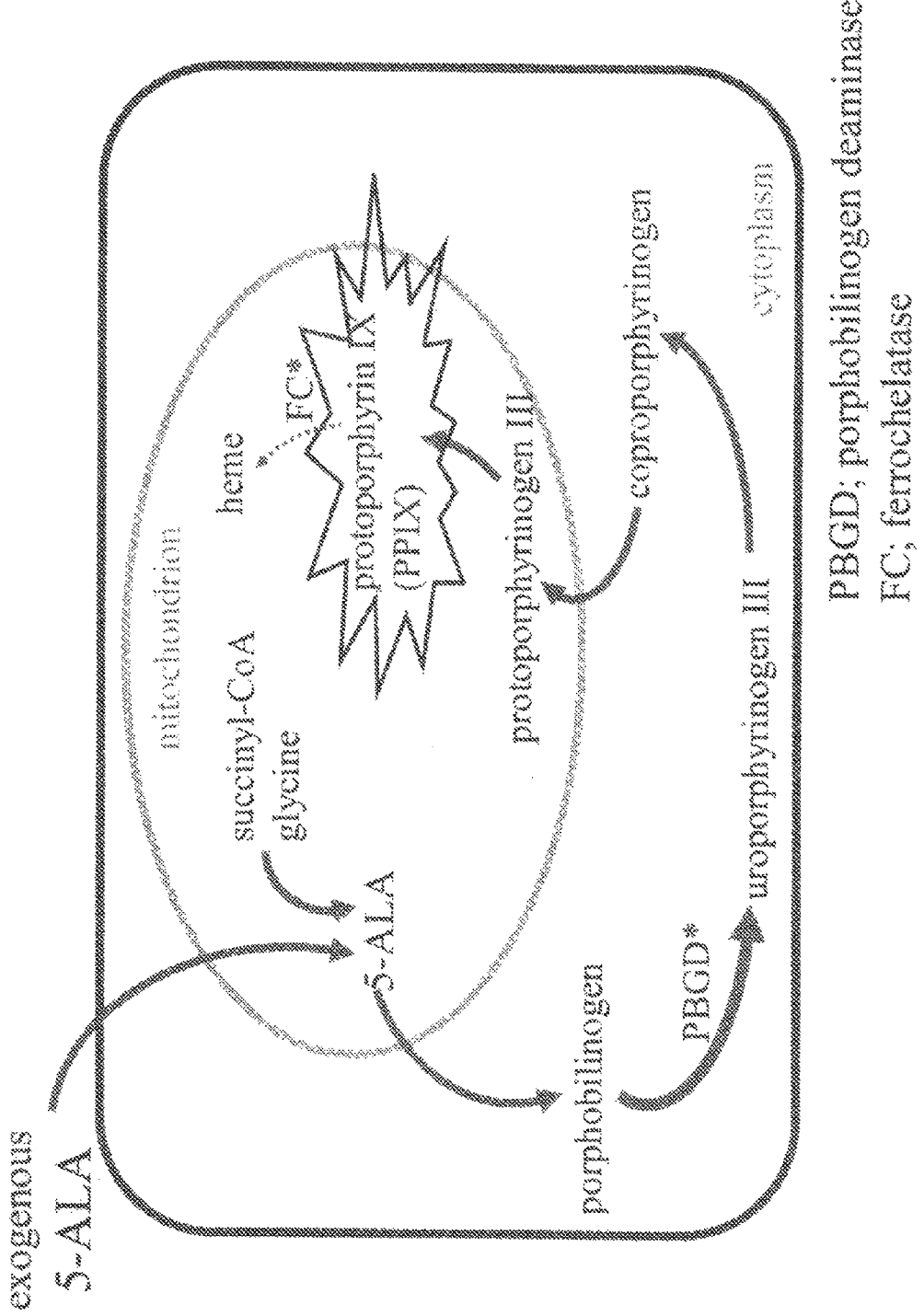
FIG. 6 shows the heme metabolic pathway in a cancer cell.

In the present invention, 5-aminolevulinic acid (5-ALA) is administered to a subject (i.e., a cancer patient). 5-ALA is absorbed into cells and converted into porphobilinogen within the cells. The porphobilinogen is then converted into a tetrapyrrole derivative, which is a tetramer of porphobilinogen, by the action of porphobilinogen deaminase (PBGD). The tetrapyrrole derivative is cyclized to give uroporphyrinogen III. The uroporphyrinogen III is then converted into protoporphyrin IX (PpIX) via coproporphyrinogen and protoporphyrinogen III (FIG. 6).

Figure 7:
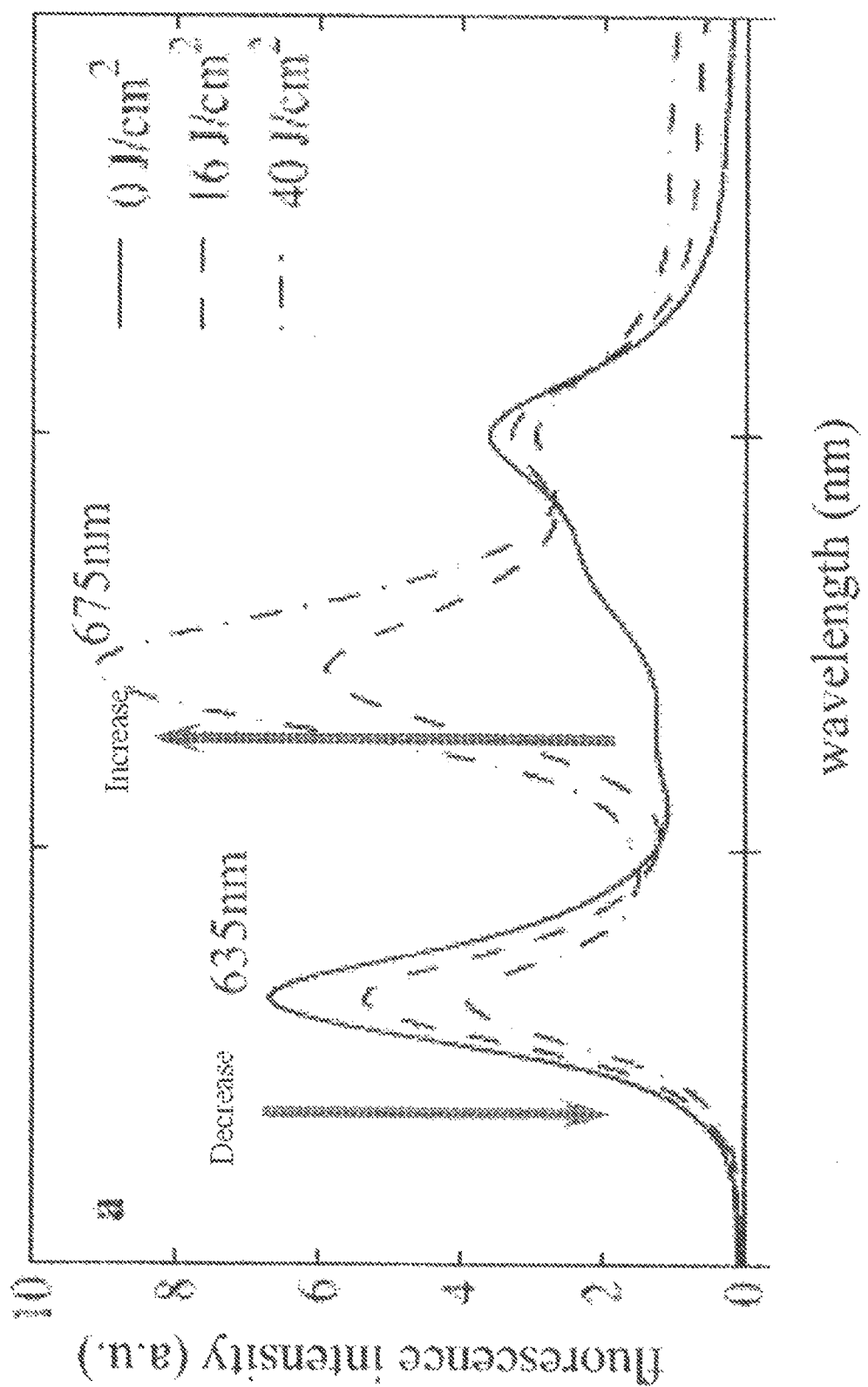
FIG. 7 shows spectral changes when PPp is gradually produced by light irradiation of PpIX. It is found that, due to light irradiation, the PpIX-derived fluorescence intensity peak at around 635 nm decreases, while the PPp-derived fluorescence intensity peak at around 675 nm increases. Ericson M B, Grapengiesser S, Gudmundson F, et al., Laser. Med. Sci., 2003, 18, 56-62

Since cancer cells have high activity of PBGD and low activity of ferrochelatase (FC) for the conversion of PpIX into heme, PpIX accumulates in cancer cells. PpIX also accumulates in the parathyroid gland. The accumulated PpIX is partially converted into PPp by light irradiation. The wavelength of light to be irradiated to convert PpIX into PPp may be in the range of about 380 to 450 nm. It is preferable to irradiate PpIX with light at a wavelength of around 436 nm so that PpIX is gradually converted into PPp (FIG. 7). The conversion of part of PpIX into PPp and the excitation of both PpIX and PPp can be performed simultaneously by irradiation with light at around 436 nm. Light at around 405 nm can also excite PpIX and PPp simultaneously; however, the yield of PPp relative to the amount of PpIX is low. Thus, in order to efficiently excite PPp to obtain fluorescence, it is preferable to apply light at around 436 nm, which is suitable for the excitation of PPp. The most preferable combination is that of irradiation light at 405 nm and excitation light at 436 nm. This combination results in the largest $I_{675}/I_{635}$ ratio. The irradiation time is about 2 to 5 minutes, and the irradiation intensity is about 2 to 5 J/cm$^2$. The irradiation time is not limited and can be shorter (e.g. shorter than 2 minutes, such as 30 seconds, 1 minute), especially in cases when the irradiation intensity is high. Irradiation with a large amount of excitation light increases the degree of conversion of PpIX into PPp, which facilitates the identification of tumor or the parathyroid gland. However, in order to identify the tumor site or the parathyroid gland during surgery, it is preferable to apply, for a short period of time, excitation light of energy that does not damage tissues and cells.

Figure 8:
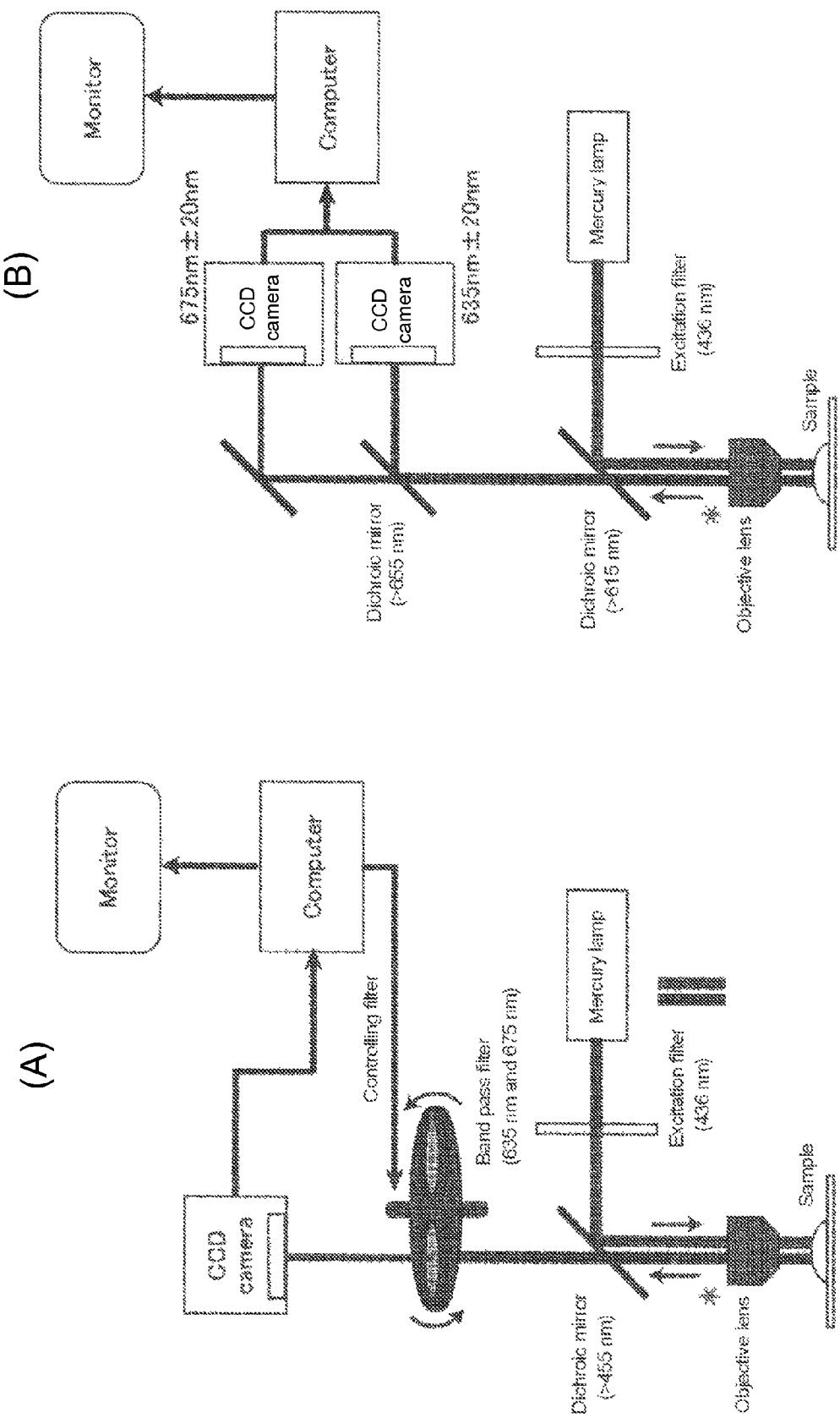
FIG. 8 shows schematic views of the device of the present invention. (A) is a method of continuously obtaining two images. Images are obtained by switching a rotating-type filter (lower figure) or a sliding-type filter, and image calculation is performed on a computer. (B) is a method of simultaneously obtaining two images. Two spectroscopic images are obtained at the same time using two CCD cameras, and image calculation is performed on a computer. When glass fibers are provided hereafter (shown by *) towards the tip of the objective lens, the device of the present invention can be used as an endoscope for in vivo diagnosis.

FIG. 8 schematically shows an embodiment of the device of the present invention. FIG. 8 is just an example of the device of the present invention, and it is obvious that the device of the present invention is not limited thereto.

In the device of FIG. 8, light from a light source (a mercury lamp in this figure) is converted into excitation light at around 436 nm by an excitation filter, and the excitation light is applied to a sample. Although FIG. 8 shows a case of using excitation light at around 436 nm, it is more preferable to combine irradiation light at around 405 nm and excitation light at around 436 nm.

The wavelength of excitation light is appropriately selected so that PpIX can be converted into PPp, and so that PPp fluorescence and PpIX fluorescence can be obtained. In the case of surgical resection of cancer, examples of the sample include lymph nodes of a cancer patient, an area of predicted metastasis such as peritoneal metastasis, an area of suspected cancer, the surroundings, and surgical margins of the resected cancer tissue. The resected cancer tissue can also be used as the sample.

The light source for the conversion of PpIX into PPp and the light source for the excitation of PpIX and PPp may be different, but are preferably the same. Examples of such a light source include mercury lamps, such as low-pressure mercury lamps, high-pressure mercury lamps, and ultra-high pressure mercury lamps; xenon lamps, halogen lamps, metal halide lamps, etc. LEDs (light emitting diodes) and laser sources are also examples of a light source as well. Among these, mercury lamps are preferred.

The excitation light from the light source may be directly applied to the area of suspected tumor in the subject via an excitation filter, an objective lens, etc. In a preferred embodiment, the excitation light passing through an excitation filter is delivered through an optical fiber, and the reflected light thereof is guided to a spectroscopy unit via an optical fiber. When an optical fiber is used, the device of the present invention can also be used as an endoscope for in vivo cancer diagnosis. Alternatively, a fluorescence microscope equipped with an objective lens can be used.

The excitation light and reflected light passing through the excitation filter are preferably allowed to pass through a dichroic mirror (>455 nm in FIG. 8A).

The reflected light passing through the dichroic mirror is separated into PpIX fluorescence and PPp fluorescence by a spectroscopy unit. The spectroscopy unit may be a band pass filter (FIG. 8A, left-hand side) or a dichroic mirror (FIG. 8B, right-hand side). The band pass filter may be of a rotating- or sliding-type (FIG. 8A shows a rotating-type band pass filter). When dichroic mirrors are used, for example, a combination of two dichroic mirrors >615 nm and >655 nm enables simultaneous acquisition of two spectroscopic data at 635±20 nm and 675±20 nm.

The two data at around 635 nm and around 675 nm obtained by the spectroscopy unit are sent to a spectroscopy detection unit to obtain image data before and after light irradiation. The spectroscopy detection unit comprises one or more imaging means, such as a CCD camera. When two images are obtained continuously using a band pass filter, as shown in FIG. 8A, the spectroscopy detection unit may comprise one imaging means (e.g., a CCD camera); whereas when two images are obtained simultaneously using dichroic mirrors, as shown in FIG. 8B, the spectroscopy detection unit may comprise two imaging means.

The image data obtained by the spectroscopy detection unit are sent to a tumor discrimination unit to determine the presence of tumor, or to a parathyroid gland discrimination unit to identify the site of parathyroid gland. The tumor discrimination unit and the parathyroid gland discrimination unit comprise a central control unit (e.g., a computer) that calculates the picture signals with optical images sent from the spectroscopy detection unit.

Figure 9:
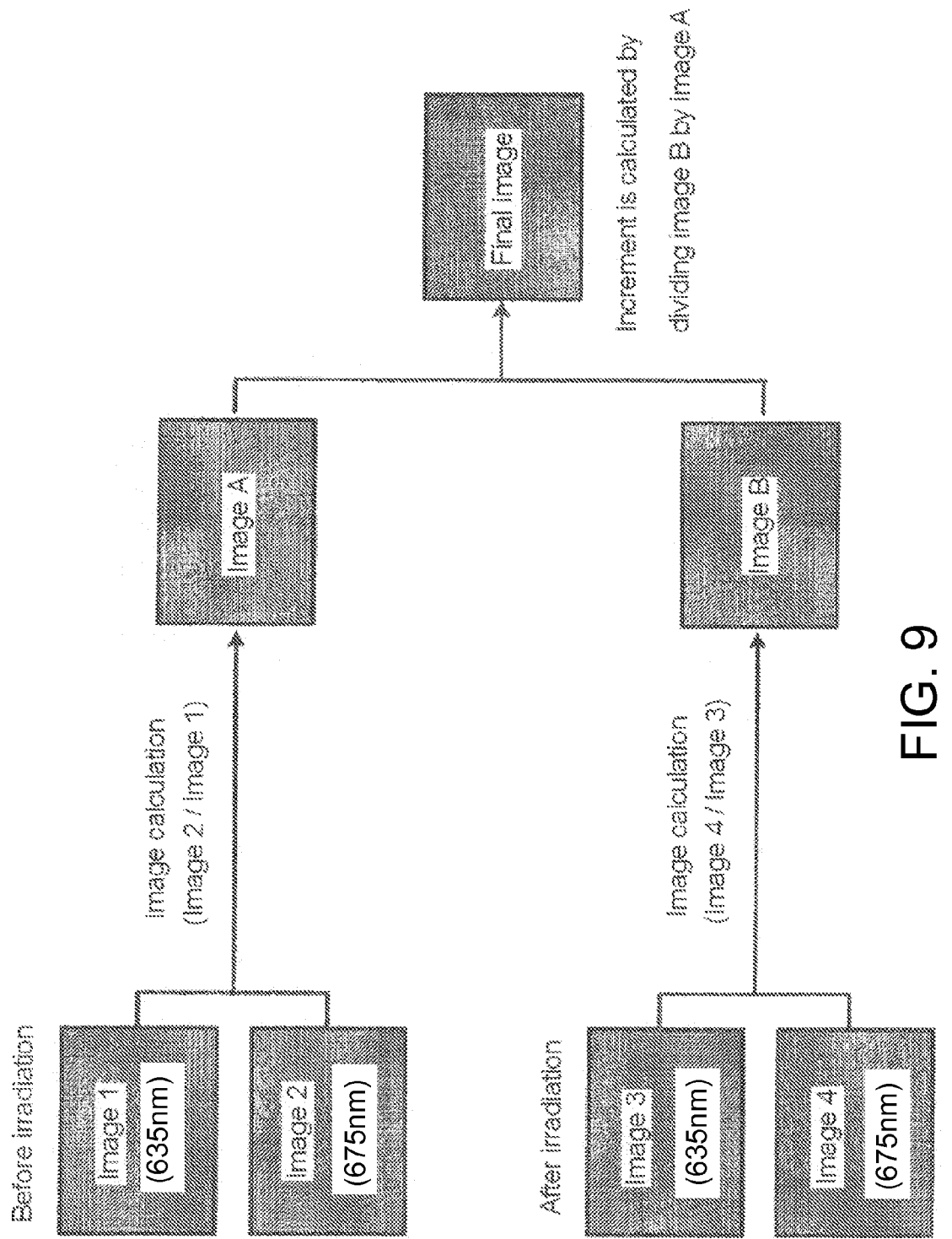
FIG. 9 shows a schematic view of image processing.

FIG. 9 shows an embodiment of calculation of two image data at 635 nm and 675 nm by the central control unit (computer). Images at 635 nm (images 1 and 3; $I_{635nm}$) and images at 675 nm (images 2 and 4; $I_{675nm}$) are obtained before and after light irradiation for the conversion of PpIX into PPp. Image calculation (division between the images: $I_{675nm}/I_{635nm}$) is performed on each pair of the images before and after light irradiation to prepare ratio images (images A and B, respectively), and the increment is calculated by dividing image B by image A. When the increment is greater than a cutoff value, the area is judged to be the tumor site, or the site of parathyroid gland; whereas when the increment is less than the cutoff value, the area is judged to be the non-tumor site, or another site other than the oarathyroid gland. More specifically, the fluorescence intensity data of the image at around 635 nm ($I_{635nm}$) and the fluorescence intensity data of the image at around 675 nm ($I_{675nm}$) are obtained. For the ratio of these data ($I_{675nm}/I_{635nm}$), ratio imaging is performed before excitation light irradiation ($I_{R\ pre}=I_{675nm\ pre}/I_{635nm\ pre}$) and after excitation light irradiation ($I_{R\ post}=I_{675nm\ post}/I_{635nm\ post}$), and the ratio ($I_{R\ post}/I_{R\ pre}$) of the ratio images ($I_{R\ pre}$ and $I_{R\ post}$) is prepared. The tumor site is visualized as an image with a high $I_{R\ post}/I_{R\ pre}$ ratio, whereas collagen, connective tissues, etc., are visualized as images with a low $I_{R\ post}/I_{R\ pre}$ ratio. Thereby, the tumor site and the site of parathyroid gland can be identified.

The determination results obtained by the tumor discrimination unit or the parathyroid gland discrimination unit can be sent to a display connected to the computer so that the tumor site or non-tumor site, or the site of parathyroid gland or another site is displayed.

The type of tumors that can be detected in the present invention is not limited. Examples thereof include tumors caused by malignant transformation of epithelial cells (i.e. cancer), such as malignant melanoma, skin cancer, lung cancer, bronchial cancer, esophageal cancer, gastric cancer, colon cancer, rectal cancer, bowel cancer, liver cancer, bile duct cancer, kidney cancer, pancreatic cancer, prostate cancer, breast cancer, uterine cancer, ovarian cancer, bladder cancer, and brain tumor; and tumors caused by malignant transformation of supporting tissue component cells (i.e. sarcoma), such as osteosarcoma and myosarcoma. Particularly preferred examples are gastrointestinal cancers (gastric cancer, colon cancer, rectal cancer, bowel cancer, pancreatic cancer, liver and bile duct cancer, etc.). Specific examples are lymph node metastasis (particularly sentinel lymph node metastasis) and peritoneal metastases of gastrointestinal cancers.

Examples of the subject include mammals, such as humans, monkeys, cows, horses, pigs, dogs, and cats; particularly humans.

Salts of 5-ALA are also usable. Examples of such salts include acid addition salts, such as hydrochloride, hydrobromate, hydroiodate, phosphate, nitrate, sulfate, acetate, toluenesulfonate, succinate, oxalate, lactate, tartrate, glycolate, methanesulfonate, citrate, fumarate, maleate, and malate; alkali metal or alkaline earth metal salts, such as sodium salt, potassium salt, and calcium salt; and the like.

The dosage of 5-ALA may be about 1 mg to 400 mg, preferably about 10 mg to 40 mg, per kg of human body weight.

The time between the administration of 5-ALA and irradiation with excitation light for exciting PpIX is preferably a time that allows accumulation of sufficient PpIX in the tumor tissues or the parathyroid gland. The specific time is 4 hours to 8 hours, for example.

EXAMPLES

The present invention is described in more detail below with reference to Examples; however, the technical scope of the present invention is not limited to these Examples.

The following materials were used in this example.

PpIX solution: PpIX was dissolved in dimethylsulfoxide (DMSO) to a concentration of 0.1 mM.

Cell line: MKN-45 (established from human poorly differentiated gastric carcinoma)

(1) Administration of 5-ALA

5-ALA (1 mM) was added to a culture dish, and the dish was incubated for 30 minutes. The medium was then replaced with fresh medium, followed by incubation for 3 hours. After trypsin treatment, a cell suspension with a concentration of $1 \times 10^7$ cells/ml was collected and used in the experiment.

(2) Spectral Analysis

Spectral analysis was performed using the following devices.

Fluorescence stereoscopic microscope (SZX12; Olympus)
Intensified multichannel spectrophotometer (MCPD-7000; Otsuka Electronics, Osaka, Japan)
Mercury lamp (U-LH100HG; Olympus)
Excitation/emission filters (D436/20x-E455LPV2)
(Ex: 436±20 nm, Em: >455 nm; Chroma Technology Corp.)

(3) Acquisition of Spectroscopic Image

Spectroscopic images were acquired using the following devices.

Macrozoom microscope (MVX10; Olympus)

12-bit monochrome CCD camera (ORCA-ER, Hamamatsu Photonics)

Liquid crystal tunable filter (Varispec VIS-20-HC-20; CRi Inc.)

Fluorescence mirror unit (U-MNBV2, Olympus)

First, background noise images ($I_{N\,635nm}$, $I_{N\,675nm}$) were taken before the acquisition of spectroscopic images.

Spectroscopic images corresponding to PpIX and PPp ($I_{S\,635nm}$, $I_{S\,675nm}$) were taken at regular time intervals.

(4) Preparation of Ratio Image

Image processing was performed using Image-J software.

Ratio images before and after irradiation ($I_{R\,0}$, $I_{R\,n}$) were prepared by the following formula:

$$I_R(t) = \frac{(I_S 675\ \text{nm}(t) - I_N 675\ \text{nm}(t))}{(I_S 635\ \text{nm}(t) - I_N 635\ \text{nm}(t))}\ (t=0, n)$$

(5) Preparation of PpIX-Specific Image

The obtained ratio images were subjected to division by the following formula:

$$I_{P_{pIX}} = \frac{I_R(n)}{I_R(0)}$$

From the results of the calculation, an area where the obtained value is greater than a certain cut-off value is the location of PpIX.

Example 1

Figure 10:
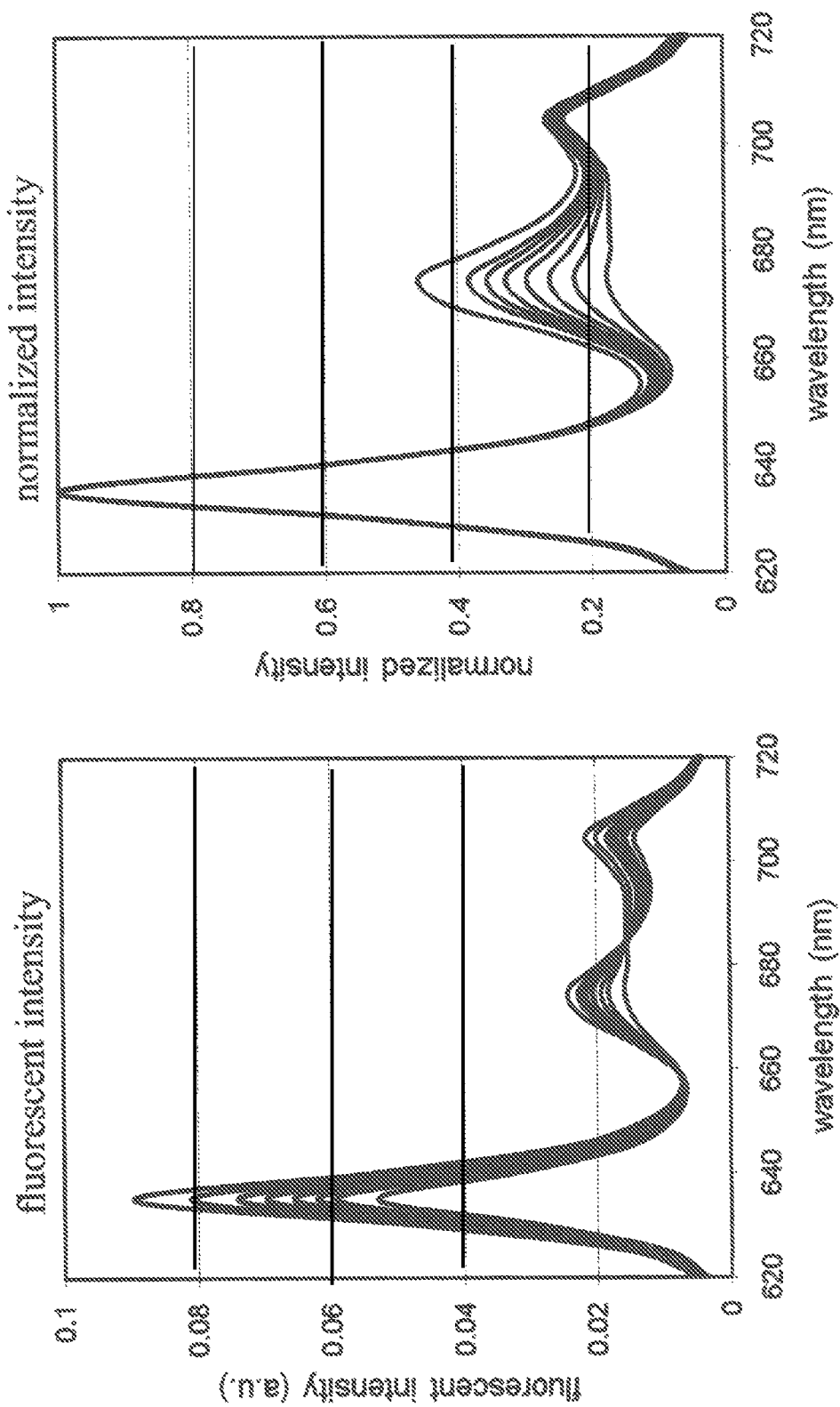
FIG. 10 shows spectral changes in 5-ALA-administered cancer cells due to light irradiation.
Figure 11:
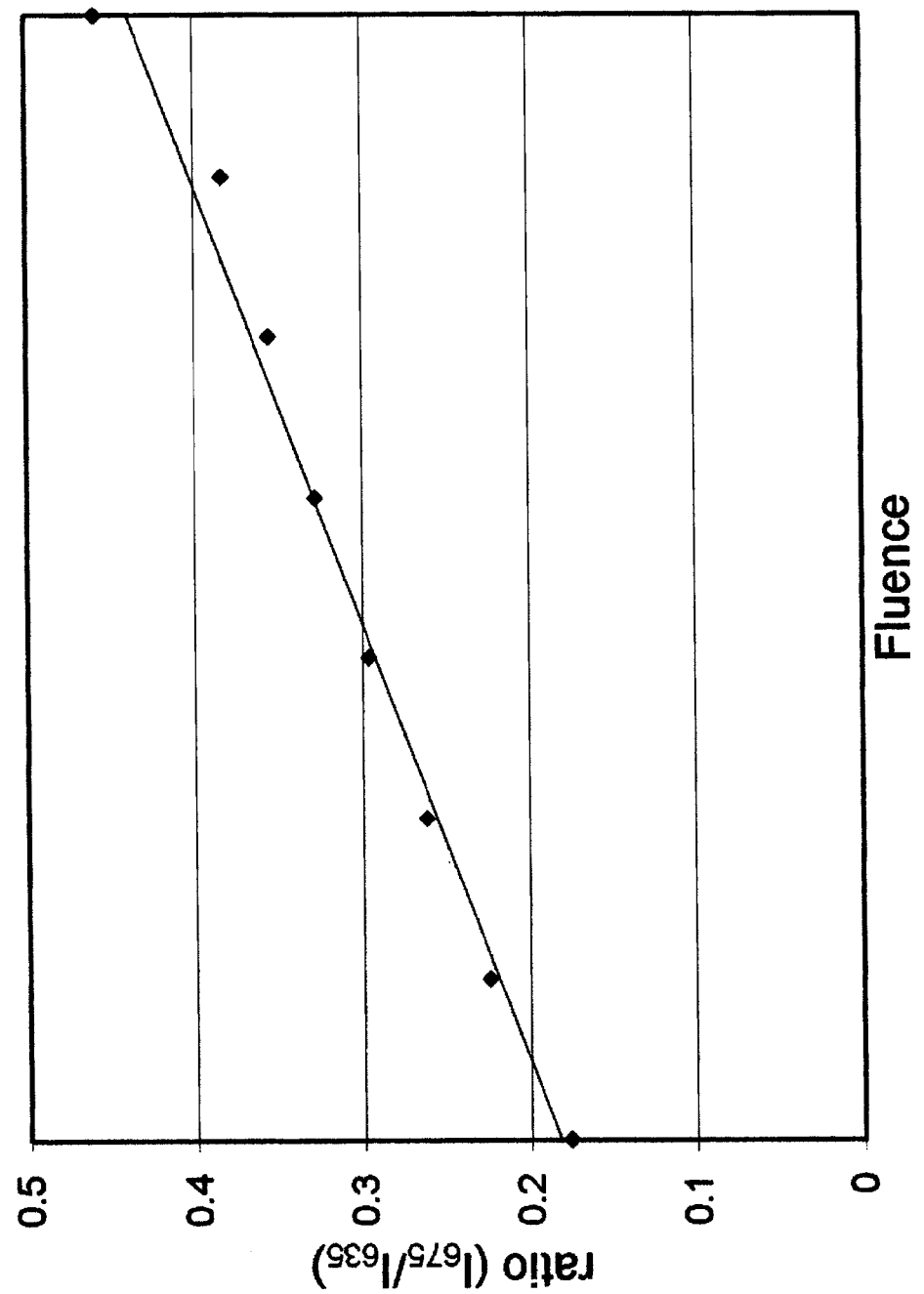
FIG. 11 shows changes in the $I_{675}/I_{635}$ ratio in 5-ALA-administered cancer cells due to light irradiation.

A gastric cancer cell line (MKN-45) was treated with 5-ALA and cultured for 3 hours. Then, the cell line was continuously irradiated with excitation light at 436 nm, and spectra were measured at regular time intervals. Although the spectral variation was different from that of the case of using a PpIX solution, a similar tendency (decrease in the peak at 635 nm and increase in the peak at 675 nm) was also observed in the cultured cells (FIG. 10). Further, it was confirmed that the $I_{675}/I_{635}$ ratio increased in a fluence-dependent manner (FIG. 11). However, the ratio variation was less than that of the case of using the PpIX solution.

Example 2

Figure 12:
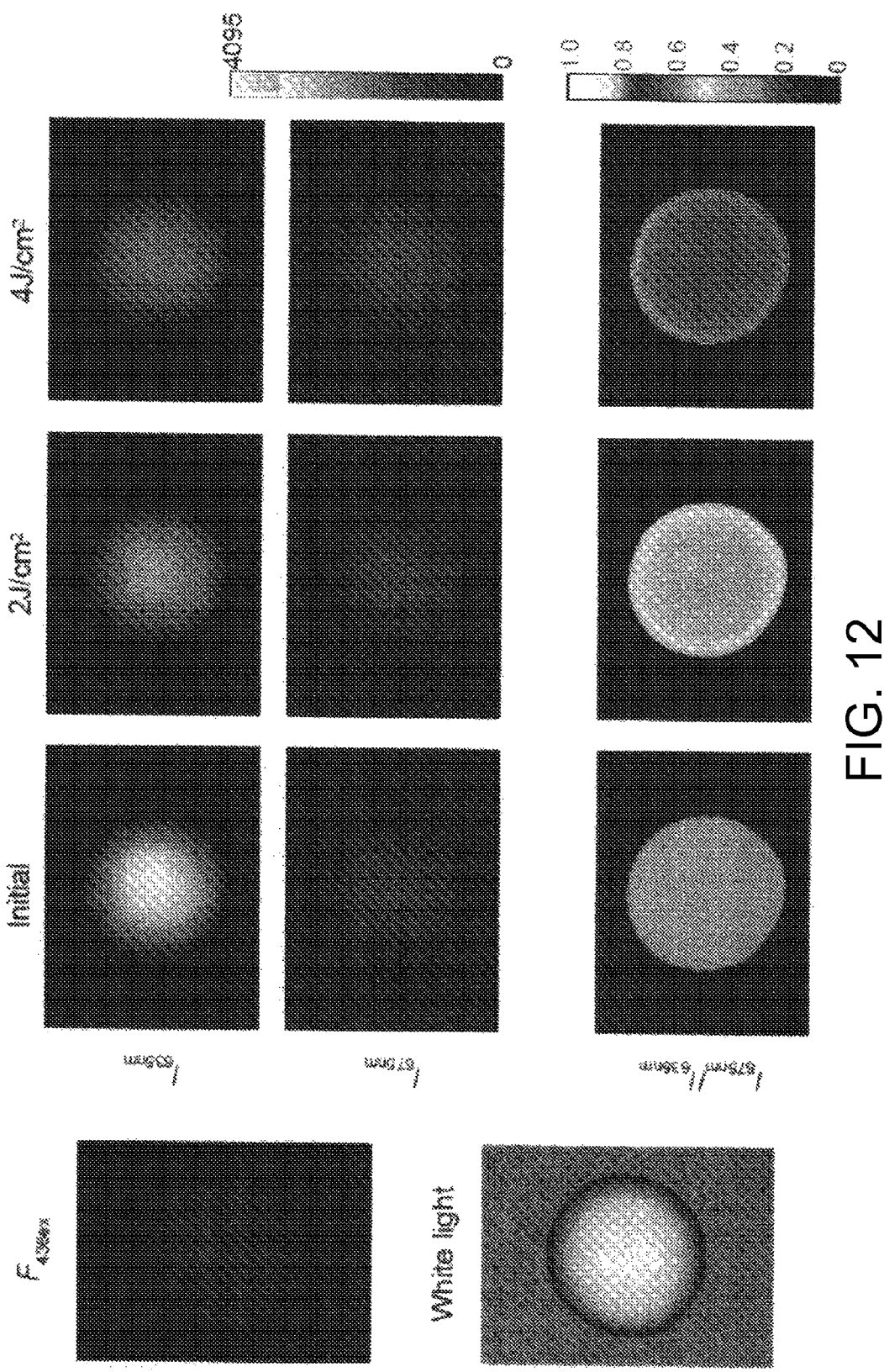
FIG. 12 shows ratio imaging of 5-ALA-administered cancer cells.

Ratio imaging was performed to visualize the spectral changes. More specifically, spectroscopic images at 635 nm and 675 nm were obtained after a fixed period of irradiation time under 436-nm excitation light, and their ratio images were prepared. Changes in the ratio images before and after irradiation were observed. FIG. 12 shows the results. Similar to the results of the spectrum measurement, it was shown that the brightness of the ratio images gradually increased along with increasing fluence.

Example 3

Ratio imaging was performed in the same manner as in Example 2 by observing collagen fibers and a cell suspension of 5-ALA-treated cancer cells at the same time.

Figure 13:
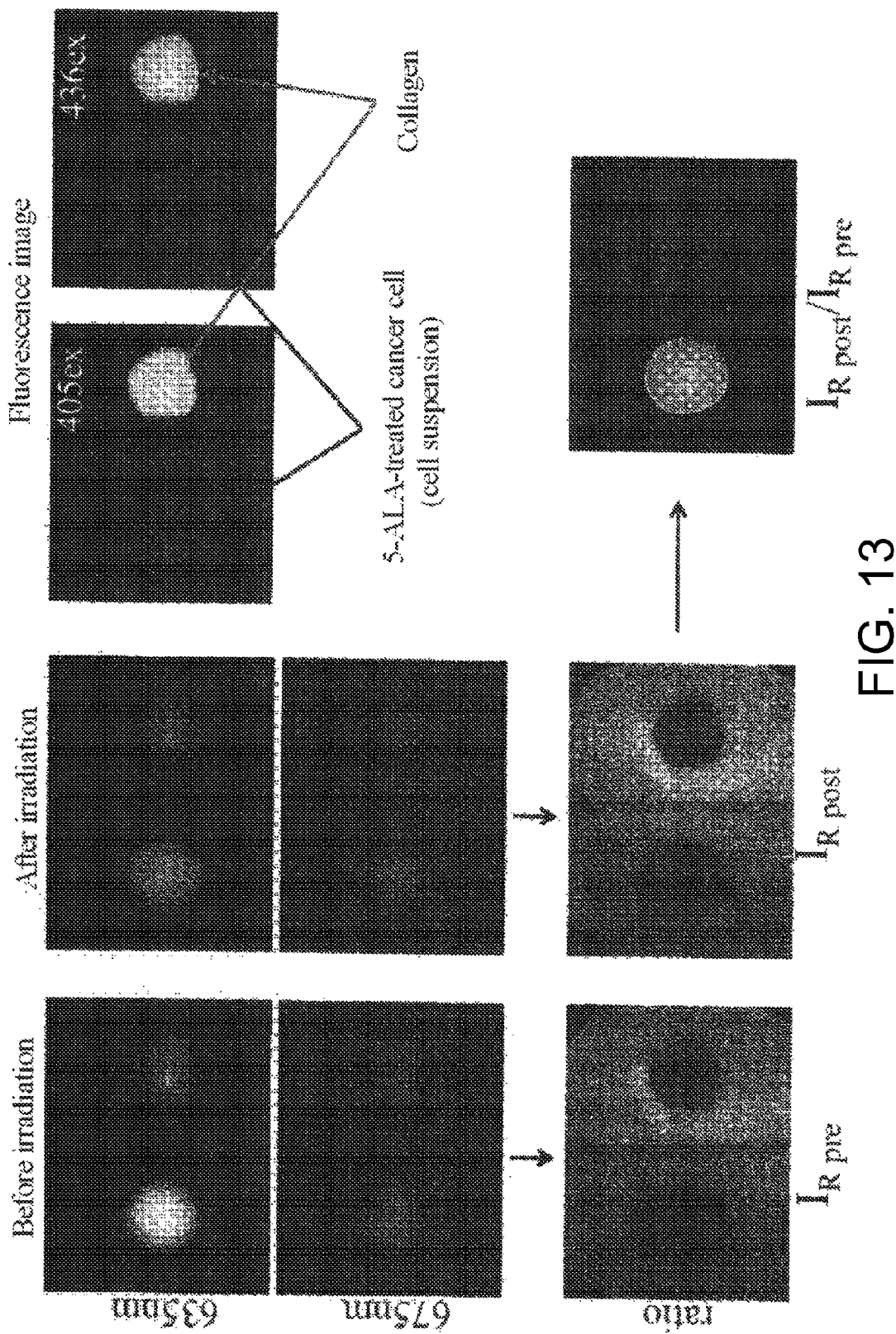
FIG. 13 shows an imaging method for specifically detecting PpIX.

The cancer cell and collagen were not distinguishable on the spectroscopic images; however, when their ratio images ($I_{R\,pre}$ and $I_{R\,post}$) were prepared, and the $I_{R\,post}/I_{R\,pre}$ ratio was calculated, it was revealed that only the location of PpIX was visualized with higher ratio value than the surrounding (FIG. 13).

Example 4

Clinical Test

Target patients were selected from gastric and colon cancer patients who were suspected of lymph node metastasis before surgery, and who agreed to participate in the clinical test in writing beforehand. However, porphyria patients, patients with an allergy history, patients with liver/kidney dysfunction, and patients with digestive tract obstruction were excluded.

Two hours before surgery, the patients received oral administration of a 50% glucose solution containing 15 mg/kg 5-ALA. Lymph nodes of an area suspected of metastasis were cut in half, and a fluorescence image and a spectroscopic image of the cross section thereof were obtained by the above-described method.

After observation, the lymph nodes were fixed in formalin, and submitted to the pathological department of the hospital for histopathological diagnosis.

Figure 14:
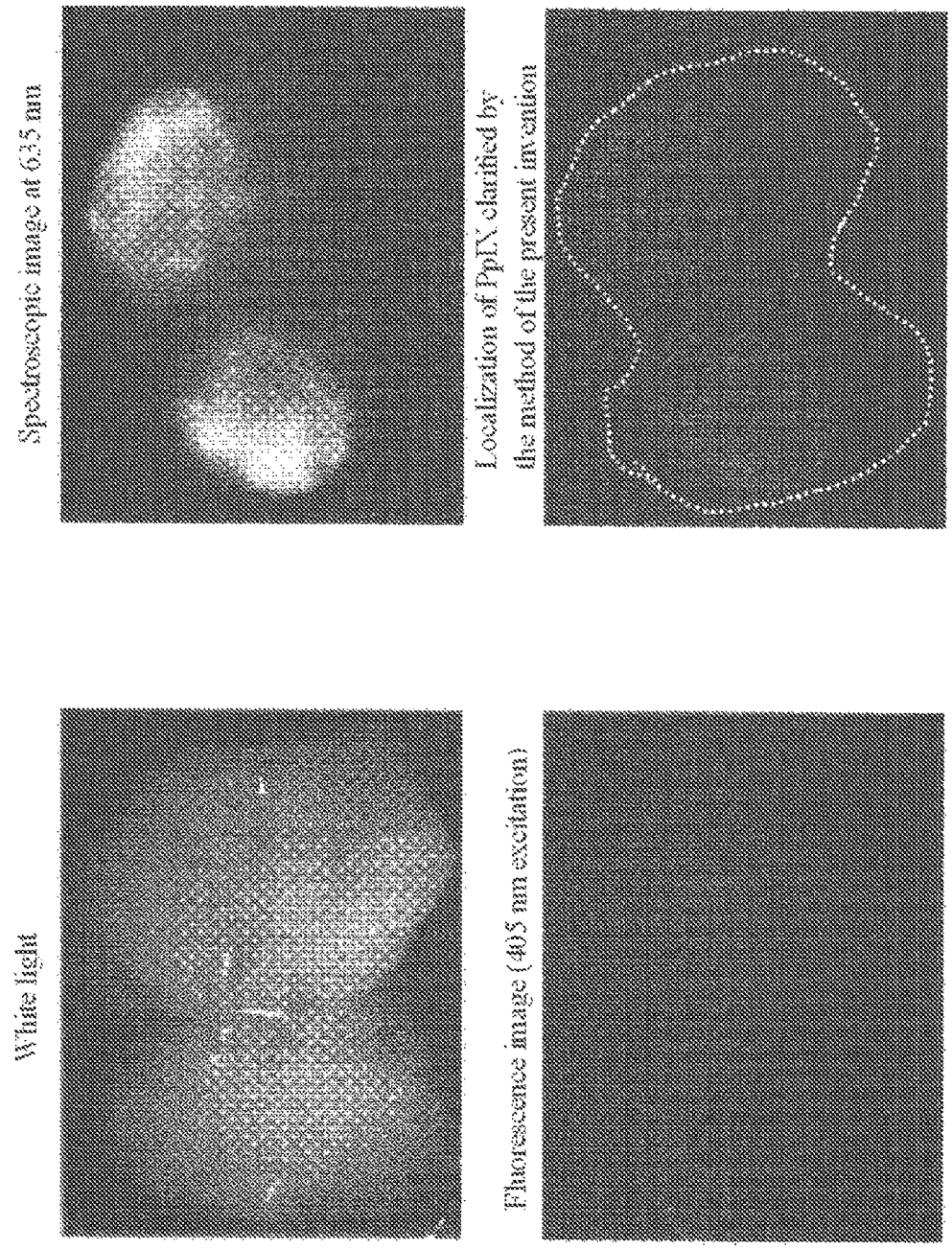
FIG. 14 shows the experimental results (1) of a clinical sample.

FIG. 14 shows the results of actual diagnosis using the tumor site identification method of the present invention.

The use of the method of the present invention allows visualization of only the location of PpIX. When the visualized image is synthesized with the original image, the actual localization of PpIX, that is, the localization of cancer, can be easily clarified.

Figure 15:
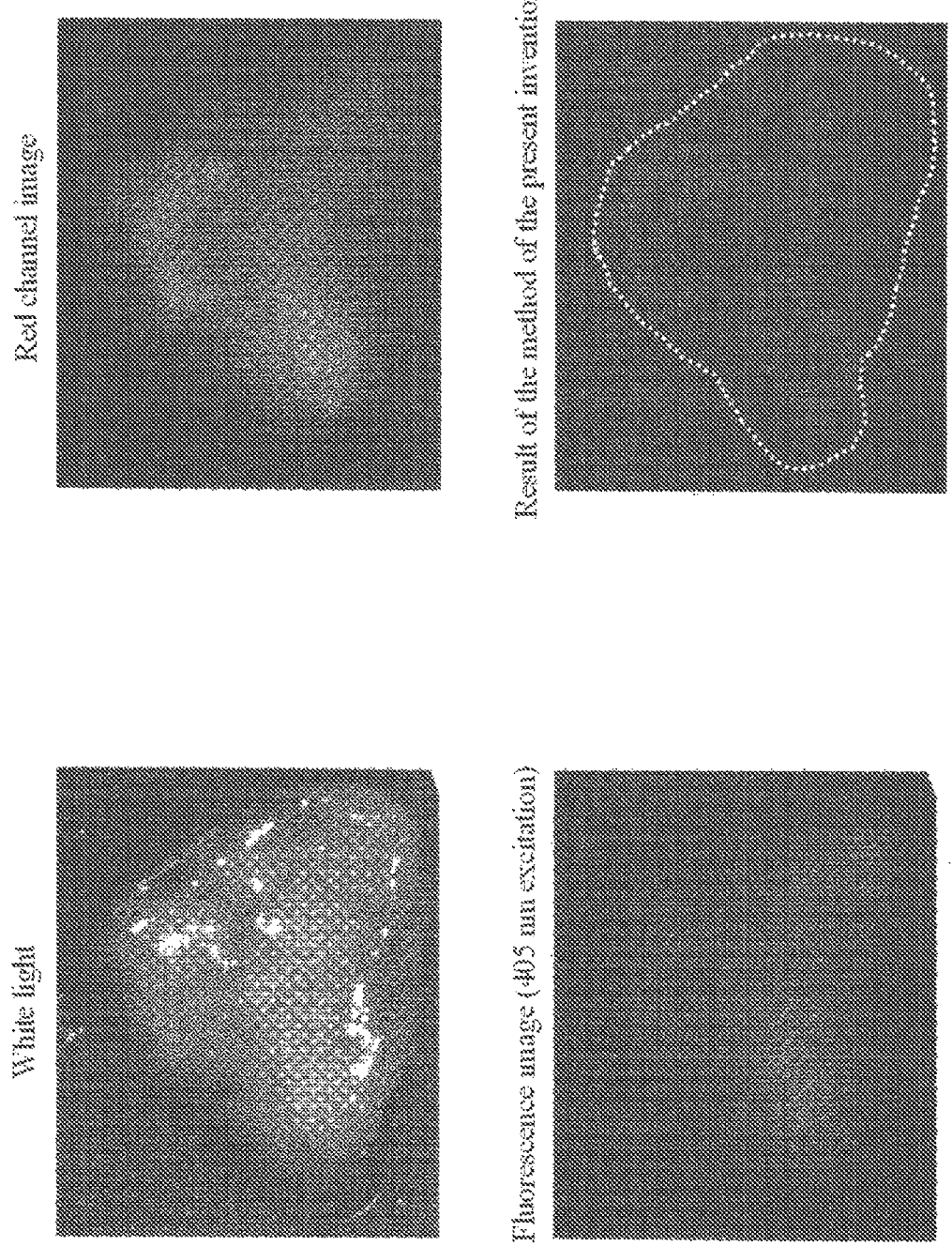
FIG. 15 shows the experimental results (2) of a clinical sample (overcoming false negatives).

Next, FIG. 15 shows the results of cancer tissues treated by the method of the present invention, to which connective tissues (e.g., collagen and fat tissue) were attached. The fluorescence image of this sample shows strong blue autofluorescence in part of the sample. Due to the impact of the autofluorescence, it was hard to confirm the red fluorescence (635 nm, 675 nm) of PpIX. Even the red channel image and the 635-nm spectroscopic image failed to clarify the localization of PpIX; however, the localization of PpIX was clarified by using the method and device of the present invention.

Figure 16:
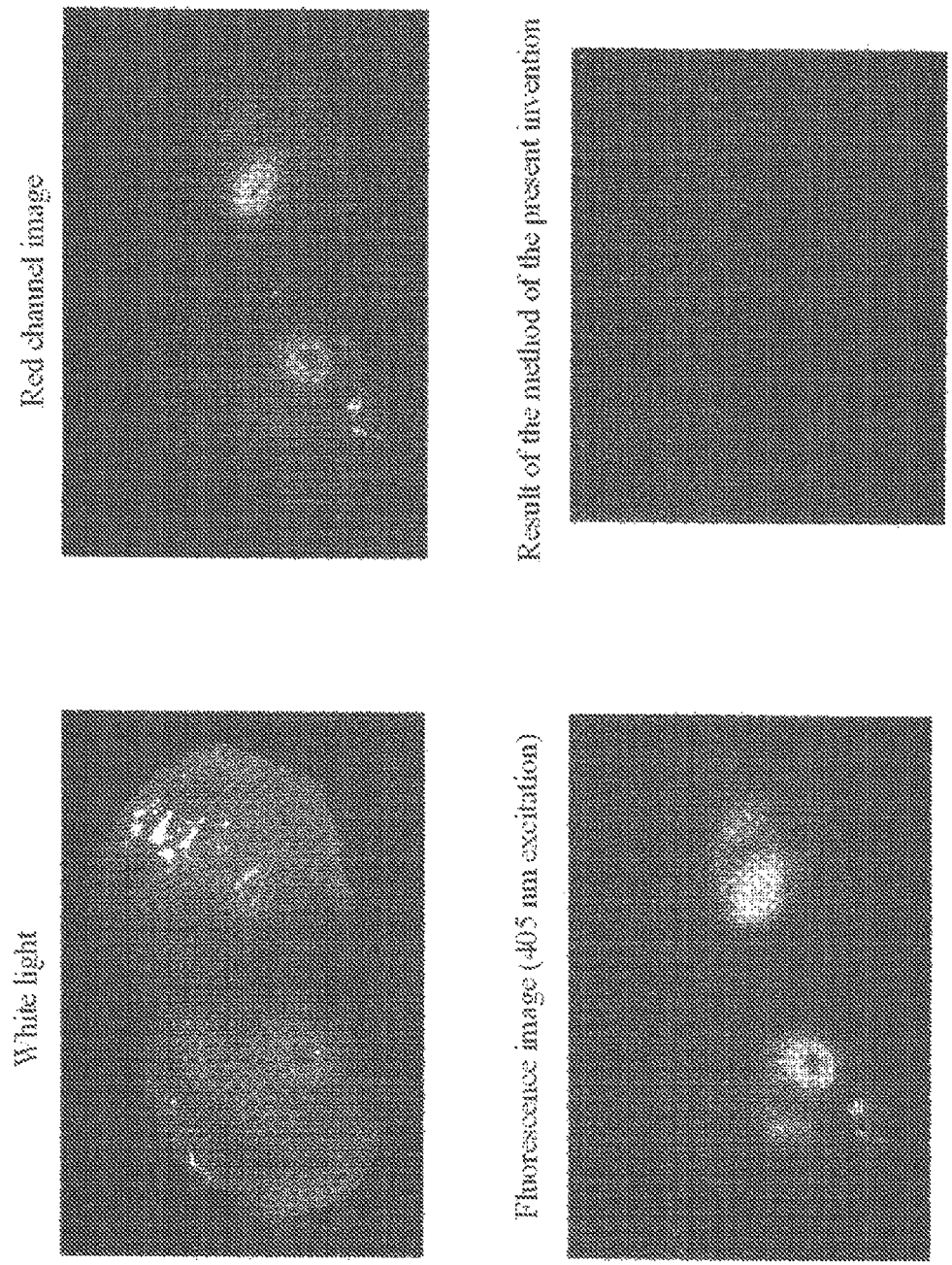
FIG. 16 shows the experimental results (3) of a clinical sample (overcoming false positives).

Furthermore, FIG. 16 shows the results of another clinical subject. In this case, strong autofluorescence derived from connective tissues and blood vessel walls was observed. Due to the impact of strong autofluorescence, the red channel image and the spectroscopic image show strong signals in areas where PpIX was not present; however, it is shown that the method and device of the present invention can eliminate the impact of autofluorescence.

Example 5

Examination of Selection of Efficient Irradiation Light

The following materials were used in this example.

(1) Cell Line

MKN-45 (established from human poorly differentiated gastric carcinoma)

(2) Administration of 5-ALA

5-ALA (1 mM) was added to a dish in which MKN-45 cells had been cultured, and the dish was incubated for 30 minutes. The medium was then replaced with fresh medium, followed by incubation for 3 hours. After trypsin treatment, a cell suspension with a concentration of 1×10⁷ cells/ml was collected and used in the experiment.

(3) Spectral Analysis

Spectral analysis was performed using the following devices.

Fluorescence stereoscopic microscope (SZX12, Olympus)

Intensified multichannel spectrophotometer (MCPD-7000, Otsuka Electronics, Osaka, Japan)

Mercury lamp (U-LH100HG, Olympus)

Excitation/emission filters (i) 405 nm excitation: D405/20x-HQ430LP (Chroma Technology Corp.)

(excitation: 405±20 nm, emission: >430 nm)

(ii) 436 nm excitation: D436/20x-E455LPV2 (Chroma Technology Corp.)

(excitation: 436±20 nm, emission: >455 nm)

(4) Conditions of Irradiation and Spectrum Acquisition

After irradiation with light at 405 nm or 436 nm, fluorescence spectra were obtained after incremental irradiation with 0.25 J/cm².

Case 1: Both Irradiation Light and Excitation Light: 405 Nm

Figure 17:
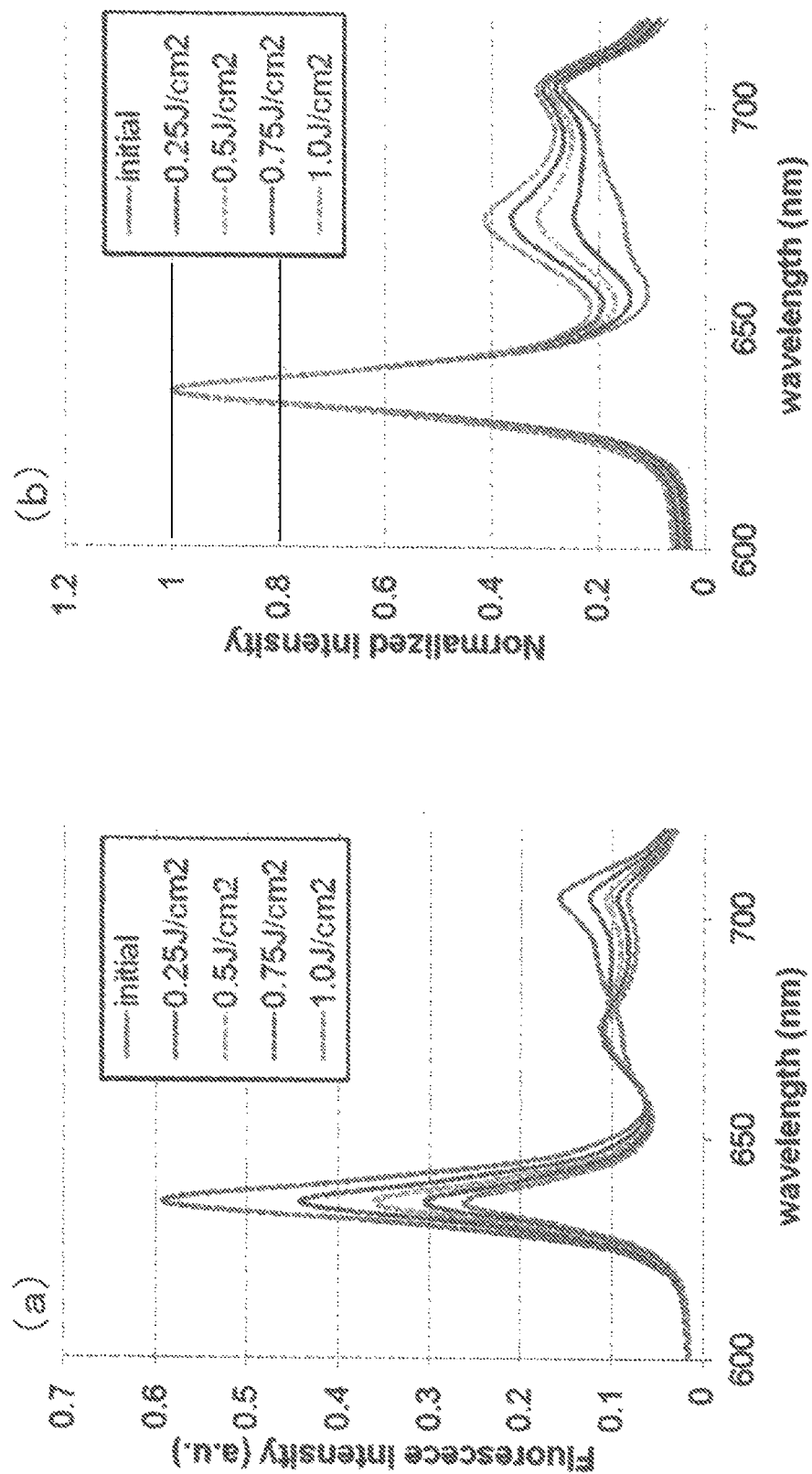
FIG. 17 shows photoconversion in 5-ALA-treated cancer cells under irradiation light at 405 nm and excitation light at 405 nm. It was revealed that the 405-nm light had a high PpIX excitation efficiency and PpIX photoconversion effect, but a low PPp excitation effect.

The 635-nm peak (PpIX) decreased along with increasing fluence, while a new peak (PPp) was observed at 675 nm (FIGS. 17 (a) and (b)).

FIG. 17 (a) is a graph showing fluorescence intensity.

FIG. 17 (b) is a graph obtained by normalizing the graph (a) by the 635-nm peak.

Case 2: Both Irradiation Light and Excitation Light: 436 Nm

Figure 18:
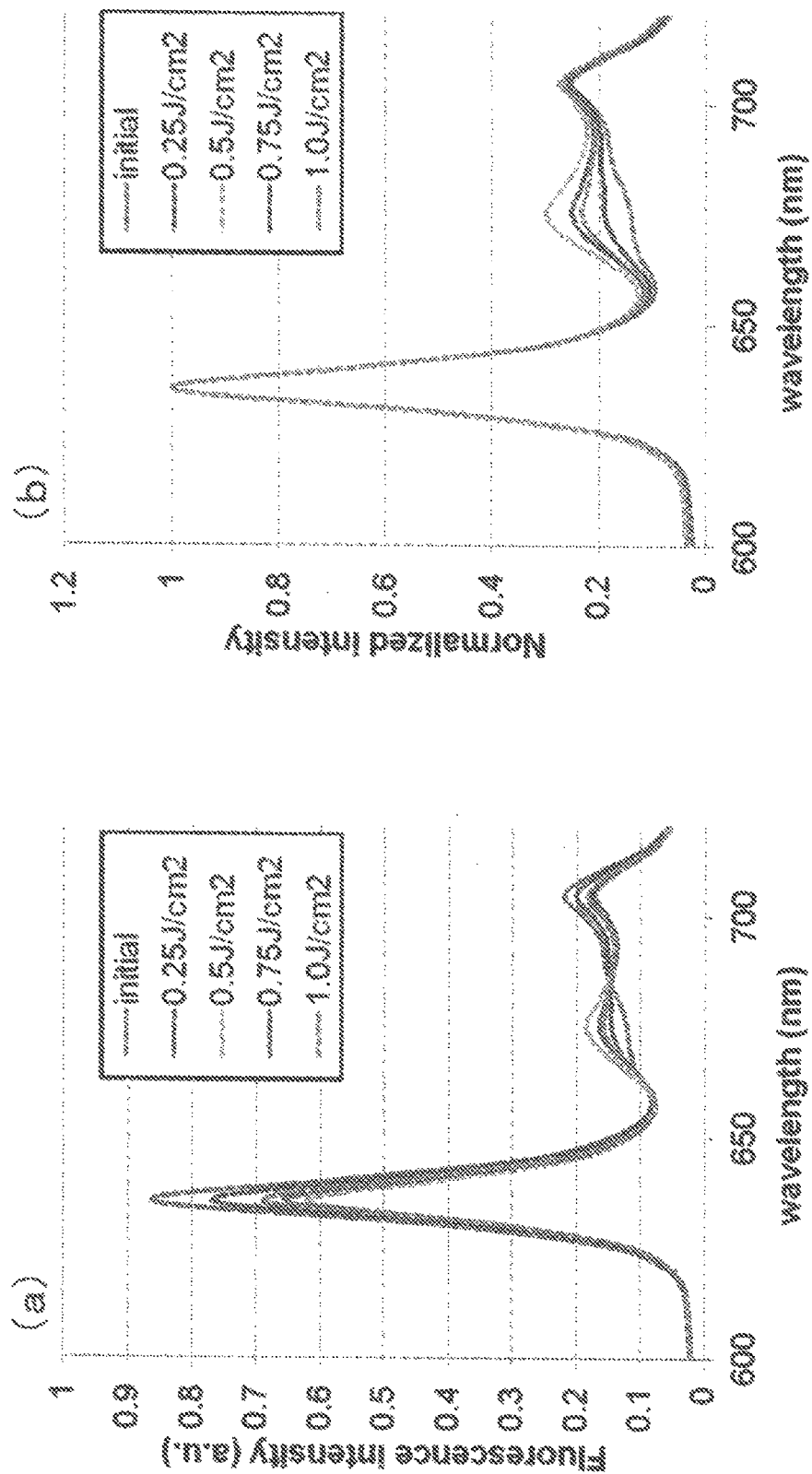
FIG. 18 shows photoconversion in 5-ALA-treated cancer cells under irradiation light at 436 nm and excitation light at 436 nm. It was revealed that the 436-nm light had a high PPp excitation efficiency, but low PpIX excitation and PpIX photoconversion effects.

The 635-nm peak (PpIX) gradually decreased along with increasing fluence, and a new peak (PPp) was observed at 675 nm (FIGS. 18 (a) and (b)).

FIG. 18 (a) is a graph showing fluorescence intensity.

FIG. 18 (b) is a graph obtained by normalizing the graph (a) by the 635-nm peak.

Case 3: Irradiation Light: 405 Nm, and Excitation Light: 436 Nm

Figure 19:
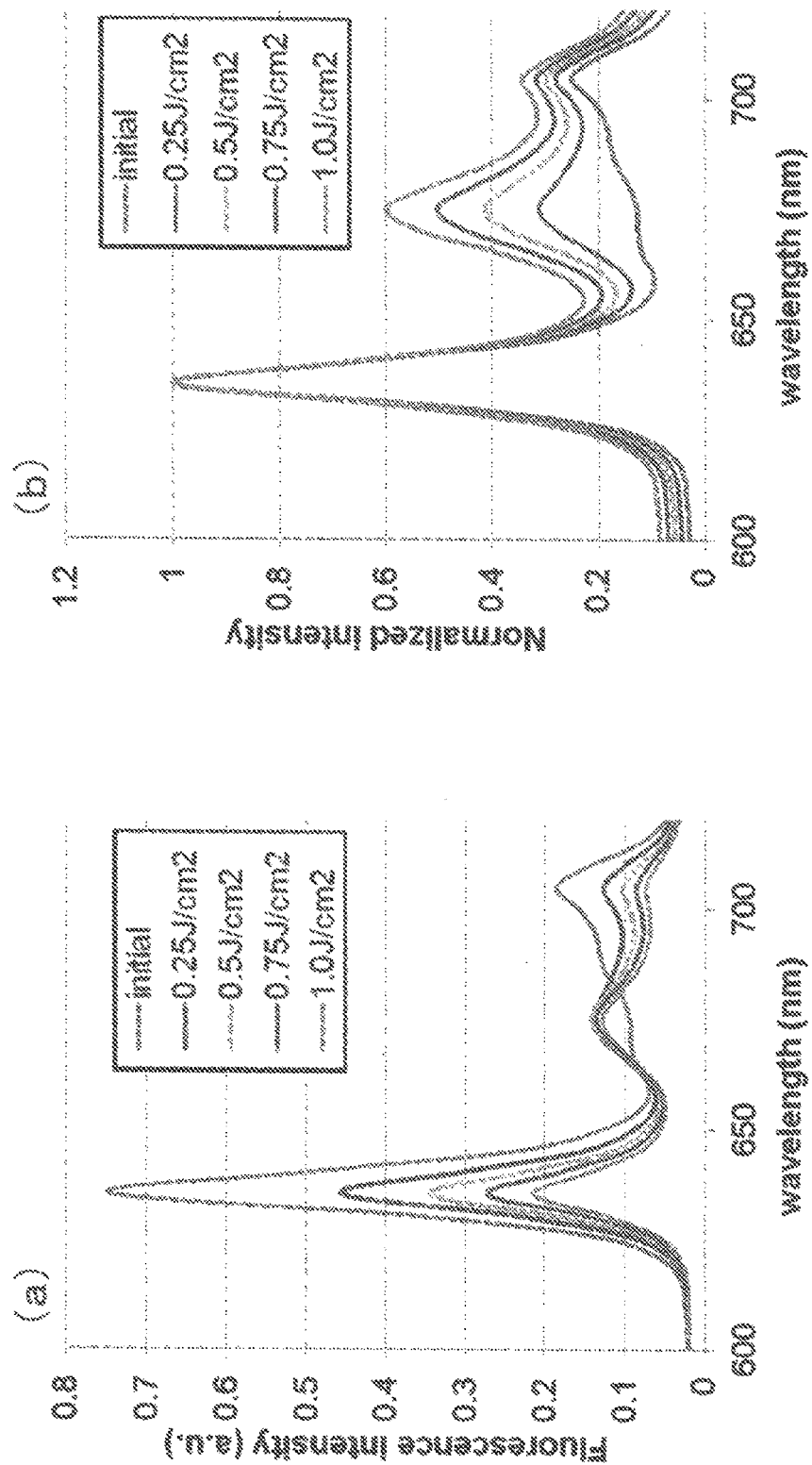
FIG. 19 shows photoconversion in 5-ALA-treated cancer cells under irradiation light at 405 nm and excitation light at 436 nm. The 405-nm irradiation light had a strong effect of photoconversion PpIX, and the 436-nm excitation light was suitable for excitation of PPp. This is thus the best combination.

The 635-nm peak (PpIX) decreased along with increasing fluence at 405 nm, and a new peak (PPp) was observed at 675 nm (FIGS. 19 (a) and (b)).

FIG. 19 (a) is a graph showing fluorescence intensity.

FIG. 19 (b) is a graph obtained by normalizing the graph (a) by the 635-nm peak.

Figure 20:
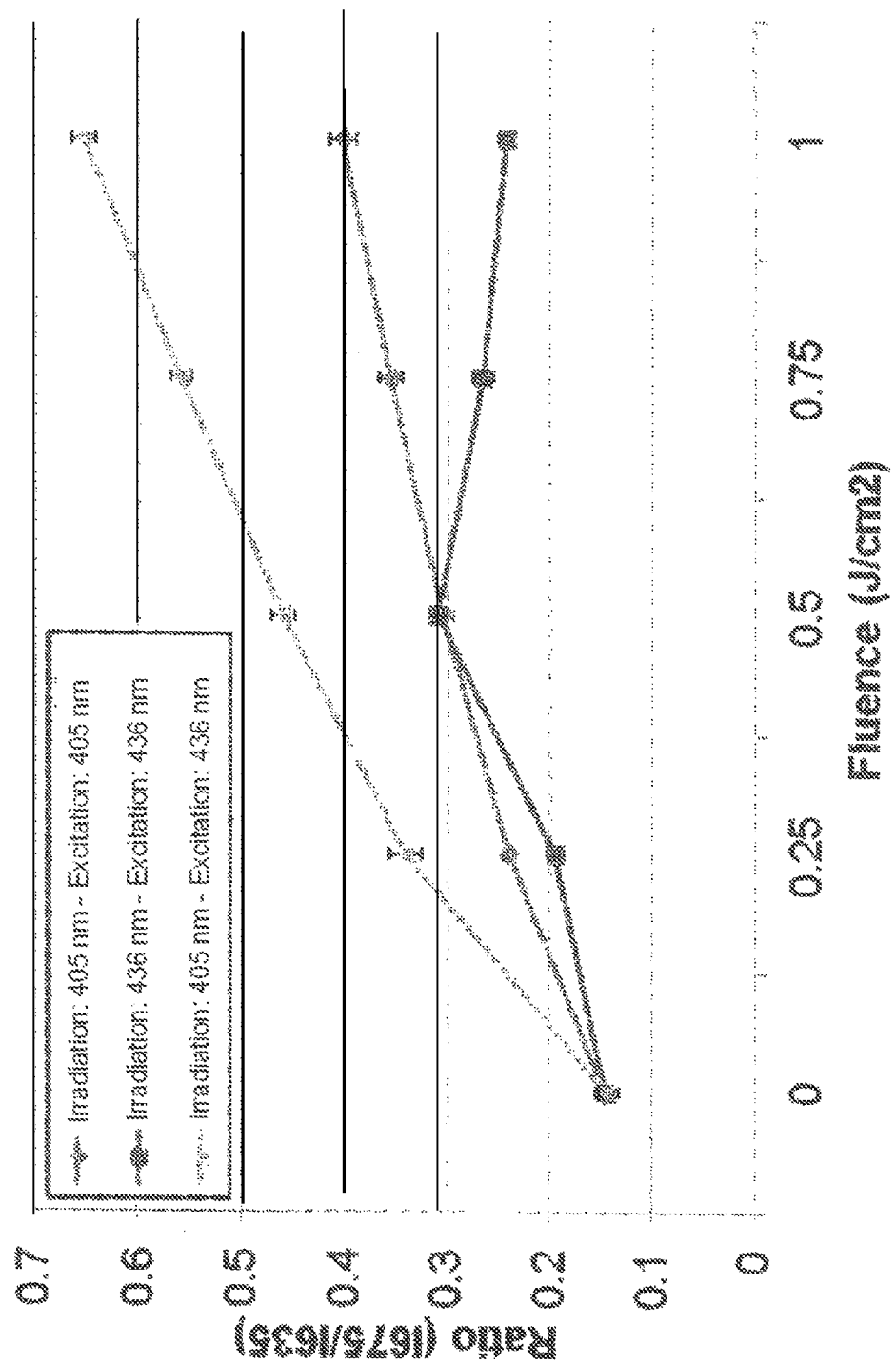
FIG. 20 shows .ratio changes due to photoconversion and light irradiation of 5-ALA-treated cancer cells. Irradiation at 405 nm and excitation at 436 nm are the best combination.

Case 4: Comparison of the Above Three Combinations (FIG. 20)

Each combination showed an increase in the $I_{675}/I_{635}$ ratio between before and after irradiation with 1 J/cm². The combination of irradiation light at 405 nm and excitation light at 436 nm (Case 3) showed the greatest change. This is because the 405-nm wavelength light can more efficiently convert PpIX into PPp, and the 436-nm excitation light is most suitable for the excitation of PPp.

Example 6

Examination of Spectral Changes in Collagen and FAD

The following materials were used in this example to examine spectral changes in typical in vivo endogenous fluorescent materials.

Collagen: Type I collagen extracted from cow's Achilles tendon

FAD: an FAD solution diluted to 90 μM

Spectral analysis was performed using the devices described above. The irradiation light was 405 nm, and the excitation light was 436 nm.

Case 1: Spectral Changes in Collagen

Figure 21:
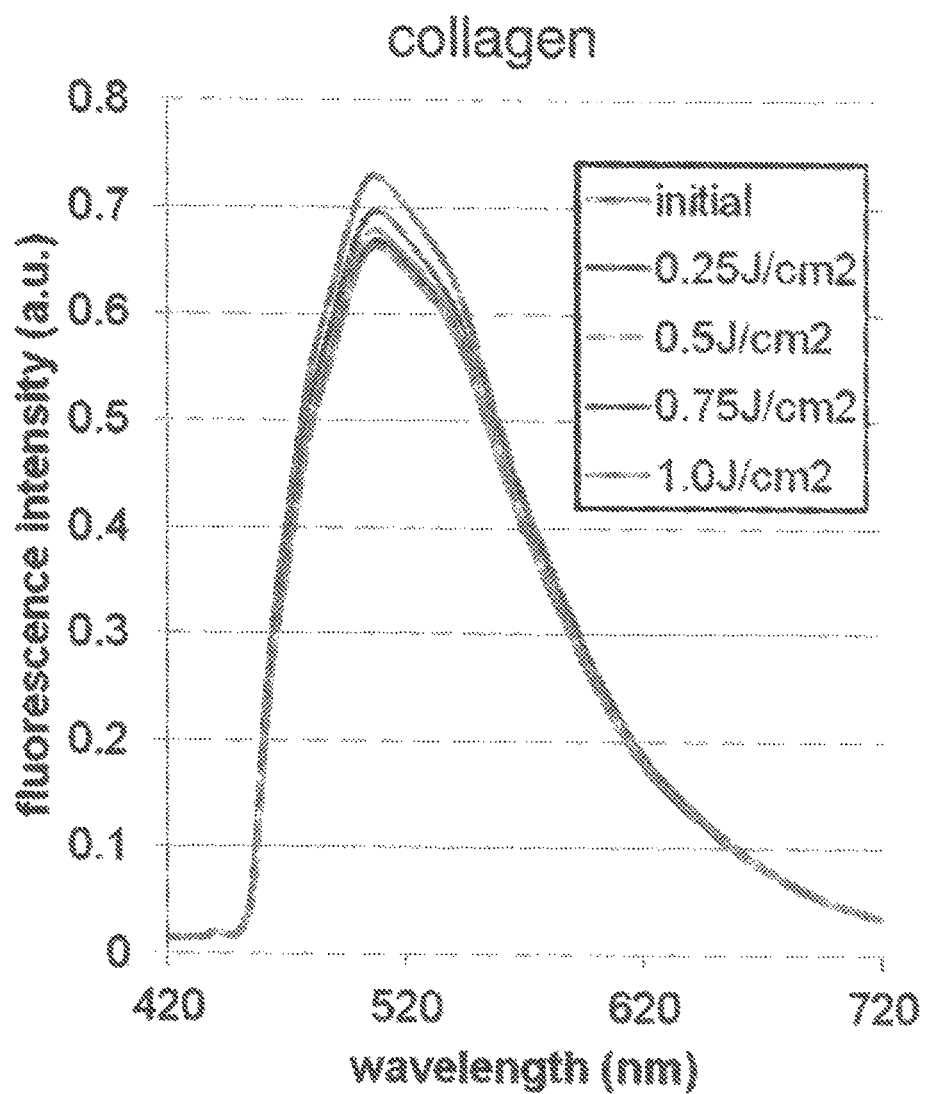
FIG. 21 shows photobleaching of collagen under irradiation light at 405 nm and excitation light at 436 nm. Almost no spectral peak shift of collagen is observed.

The entire fluorescence peak decreased along with increasing fluence; however, no change of spectral peak wavelength was observed (FIG. 21).

Case 2: Spectral Changes in FAD

Figure 22:
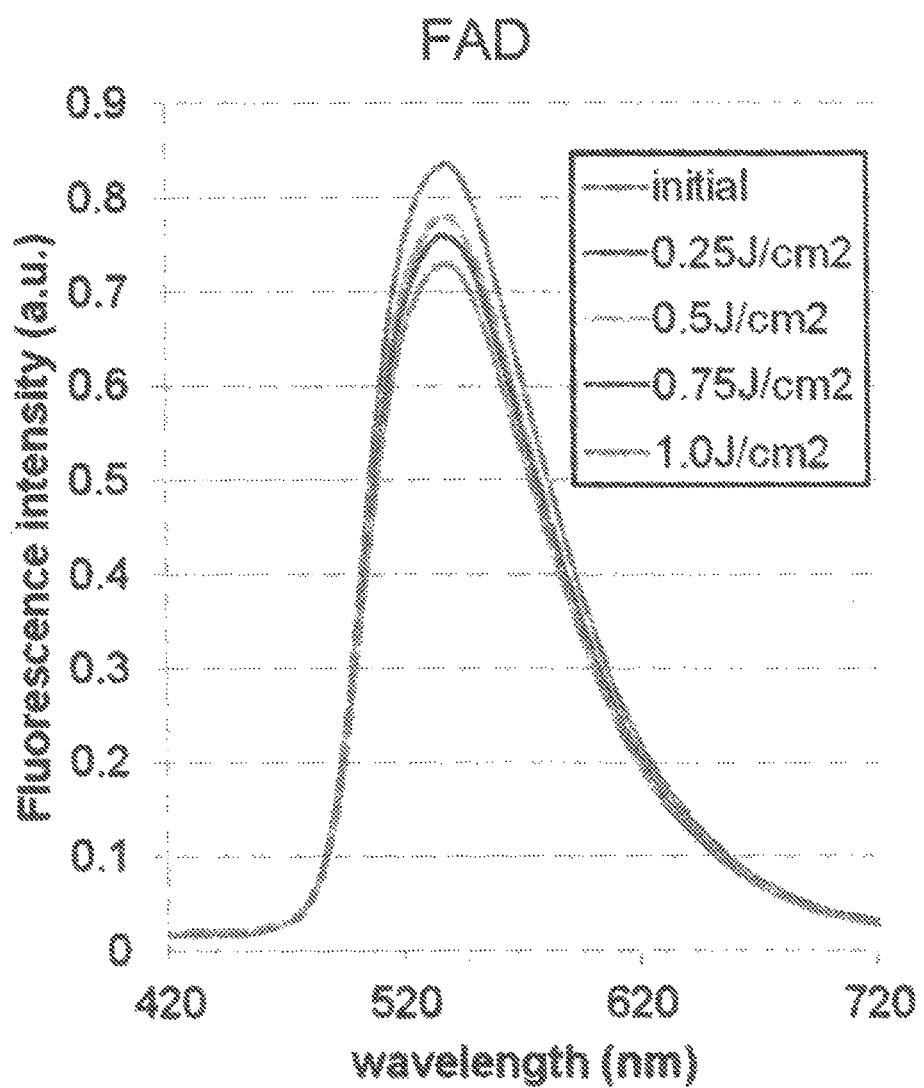
FIG. 22 shows photobleaching of FAD under irradiation light at 405 nm and excitation light at 436 nm. Almost no photobleaching of FAD is observed.

The entire fluorescence peak decreased along with increasing fluence; however, no change of spectral peak wavelength was observed (FIG. 22).

Case 3: $I_{675}/I_{635}$ Ratio Changes Along with Increasing Fluence

Figure 23:
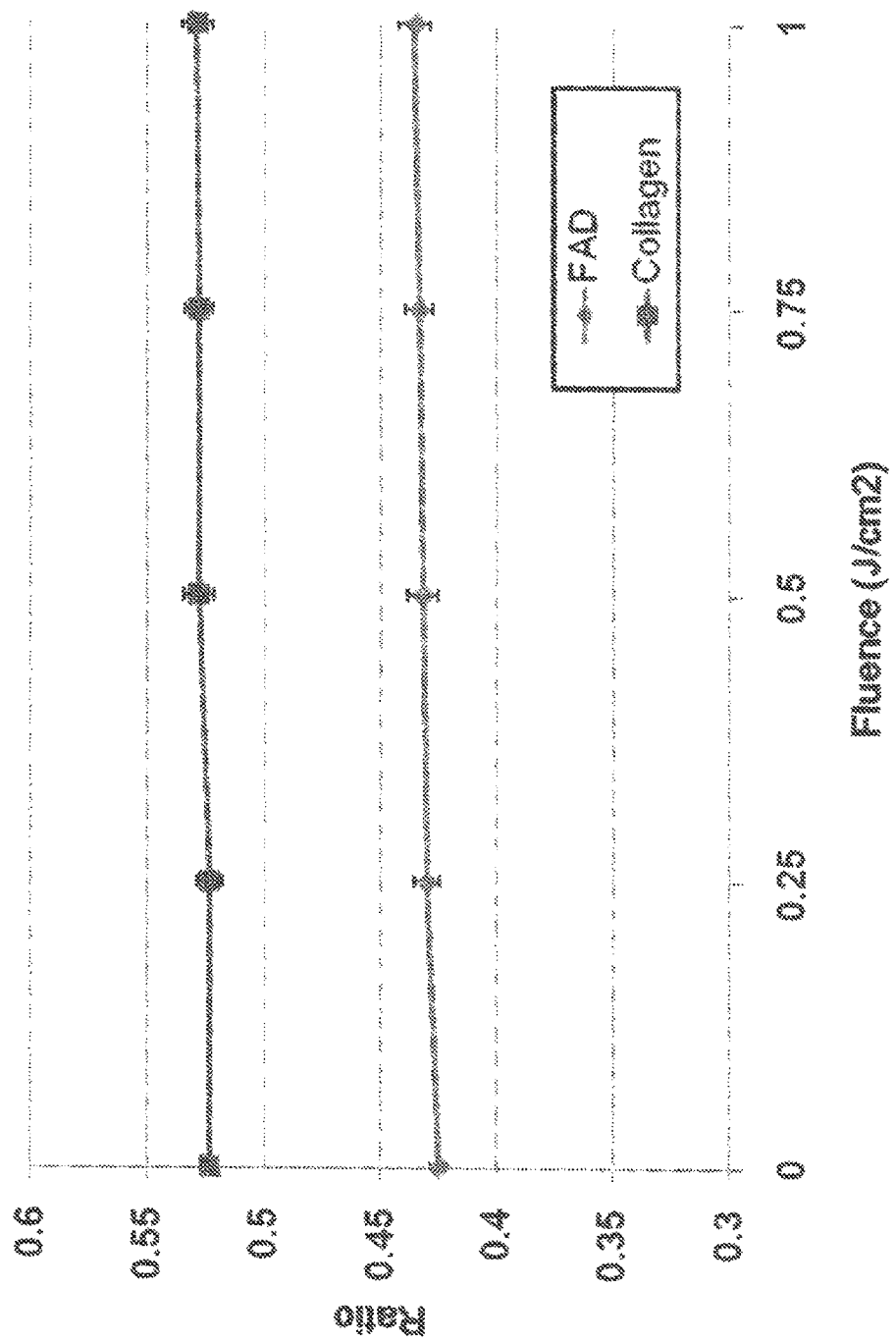
FIG. 23 shows ratio changes due to photobleaching and light irradiation for collagen and FAD. No ratio change is observed after light irradiation of collagen or FAD.

Both collagen and FAD showed almost constant ratio values after light irradiation (FIG. 23). Since these results are different from the ratio changes in PpIX, PpIX can be distinguished from collagen and FAD.

The invention claimed is:

1. A device for identifying a tumor site in a subject, the device spectroscopically detecting fluorescence of protoporphyrins present in the tumor site, the protoporphyrins being protoporphyrin IX (PpIX) and photo-protoporphyrin (PPp), and the device comprising:

a light irradiation unit configured to convert part of PpIX into PPp;

a spectroscopy unit configured to separate PpIX fluorescence and PPp fluorescence:

a spectroscopy detection unit configured to detect the relative fluorescence intensity of the PpIX fluorescence and the PPp fluorescence; and a computer configured to discriminate between the tumor site and a non-tumor site based on the relative fluorescence intensity of PpIX and PPp.

2. The device according to claim 1, wherein the light irradiation unit comprises a light source and a light source optical fiber for guiding excitation light from the light source to the subject.

3. The device according to claim 2, wherein the spectroscopy detection unit comprises a means for detecting PpIX-derived fluorescence at around 635 nm, and a means for detecting PPp-derived fluorescence at around 675 nm.

4. The device according to claim 3, comprising a spectroscopy optical fiber for guiding the PpIX fluorescence and the PPp fluorescence to the spectroscopy unit.

5. The device according to claim 4, further comprising a display unit that displays information regarding the tumor discrimination results from the computer as image information corresponding to the position of the discriminated tumor site emitting fluorescence in the subject.

6. The device according to claim 3, further comprising a display unit configured to display information regarding the tumor discrimination results from the computer as image information corresponding to the position of the discriminated tumor site emitting fluorescence in the subject.

7. The device according to claim 2, further comprising a display unit configured to display information regarding the tumor discrimination results from the computer as image information corresponding to the position of the discriminated tumor site emitting fluorescence in the subject.

8. The device according to claim 2, comprising a spectroscopy optical fiber for guiding the PpIX fluorescence and the PPp fluorescence to the spectroscopy unit.

9. The device according to claim 8, further comprising a display unit configured to display information regarding the tumor discrimination results from the computer as image information corresponding to the position of the discriminated tumor site emitting fluorescence in the subject.

10. The device according to claim 1, wherein the spectroscopy detection unit comprises a means for detecting PpIX-derived fluorescence at around 635 nm, and a means for detecting PPp-derived fluorescence at around 675 nm.

11. The device according to claim 10, further comprising a display unit configured to display information regarding the tumor discrimination results from the computer as image information corresponding to the position of the discriminated tumor site emitting fluorescence in the subject.

12. The device according to claim 10, comprising a spectroscopy optical fiber for guiding the PpIX fluorescence and the PPp fluorescence to the spectroscopy unit.

13. The device according to claim 12, further comprising a display unit configured to display information regarding the tumor discrimination results from the computer as image information corresponding to the position of the discriminated tumor site emitting fluorescence in the subject.

14. The device according to claim 1, comprising a spectroscopy optical fiber for guiding the PpIX fluorescence and the PPp fluorescence to the spectroscopy unit.

15. The device according to claim 14, further comprising a display unit configured to display information regarding the tumor discrimination results from computer as image information corresponding to the position of the discriminated tumor site emitting fluorescence in the subject.

16. The device according to claim 1, further comprising a display unit configured to display information regarding the tumor discrimination results from the computer, as image information corresponding to the position of the discriminated tumor site emitting fluorescence in the subject.

17. A method for identifying a tumor site in a subject, comprising the steps of:
irradiating protoporphyrin IX (PpIX) accumulated in the tumor site of the subject with light to convert part of PpIX into photo-protoporphyrin (PPp);
irradiating excitation light for PpIX and PPp;
separating fluorescence emitted from PpIX and PPp, which have been excited with the excitation light, into PpIX fluorescence and PPp fluorescence using a spectroscopy unit;
detecting the relative fluorescence intensity of the PpIX fluorescence and the PPp fluorescence; and
discriminating between the tumor site and a non-tumor site based on the relative fluorescence intensity of PpIX and PPp.

18. The method according to claim 17, wherein the tumor is a tumor metastasized to a sentinel lymph node.

19. A device for identifying a parathyroid gland in a subject, the device spectroscopically detecting fluorescence of protoporphyrins present in the parathyroid gland,
the protoporphyrins being protoporphyrin IX (PpIX) and photo-protoporphyrin (PPp), and
the device comprising:
a light irradiation unit configured to convert part of PpIX into PPp;
a spectroscopy unit configured to separate PpIX fluorescence and PPp fluorescence:
a spectroscopy detection unit configured to detect the relative fluorescence intensity of the PpIX fluorescence and the PPp fluorescence; and
a computer configured to discriminate between the parathyroid gland site and another site based on the relative fluorescence intensity of PpIX and PPp.

20. A method for identifying a parathyroid gland in a subject, comprising the steps of:
irradiating protoporphyrin IX (PpIX) accumulated in the parathyroid gland of the subject with light to convert part of PpIX into photo-protoporphyrin (PPp);
irradiating excitation light for PpIX and PPp;
separating fluorescence emitted from PpIX and PPp, which have been excited with the excitation light, into PpIX fluorescence and PPp fluorescence using a spectroscopy unit;
detecting the relative fluorescence intensity of the PpIX fluorescence and the PPp fluorescence; and
discriminating between the parathyroid gland and another site based on the relative fluorescence intensity of PpIX and PPp.

* * * * *